United States Patent [19]

Kikuchi et al.

[11] Patent Number: 4,884,580
[45] Date of Patent: Dec. 5, 1989

[54] HYPERTHERMIA DEVICE

[75] Inventors: Makoto Kikuchi, Mitaka; Shinsaku Mori; Yoshio Nikawa, both of Tokyo; Takashige Terakawa, Tokyo, all of Japan

[73] Assignee: Tokyo Keiki Co. Ltd., Tokyo, Japan

[21] Appl. No.: 251,973

[22] Filed: Sep. 30, 1988

Related U.S. Application Data

[63] Continuation of Ser. No. 14,138, Feb. 12, 1987, abandoned, which is a continuation of Ser. No. 707,490, Mar. 1, 1985, abandoned.

[30] Foreign Application Priority Data

| Mar. 4, 1984 | [JP] | Japan | 59-40792 |
| Mar. 4, 1984 | [JP] | Japan | 59-40793 |
| Mar. 4, 1984 | [JP] | Japan | 59-40794 |
| Mar. 4, 1984 | [JP] | Japan | 59-40795 |
| Mar. 4, 1984 | [JP] | Japan | 59-40796 |

[51] Int. Cl.[4] ................................ A61N 5/02
[52] U.S. Cl. ...................... 128/804; 128/422; 219/10.55 R
[58] Field of Search ............ 128/804, 399, 422; 219/10.55 R, 10.55 A, 10.55 B, 10.55 F

[56] References Cited

U.S. PATENT DOCUMENTS

| 3,077,195 | 2/1963 | Folsche | 128/804 |
| 4,108,147 | 8/1978 | Kantor | 128/804 |
| 4,140,130 | 2/1979 | Storm III | 128/804 |
| 4,204,549 | 5/1980 | Paglione | 128/804 X |
| 4,228,809 | 10/1980 | Paglione | 128/804 |
| 4,282,887 | 8/1981 | Sterzer | 128/804 |
| 4,341,227 | 7/1982 | Turner | 128/804 |
| 4,397,313 | 8/1983 | Vaguine | 128/804 |
| 4,397,314 | 8/1983 | Vaguine | 128/804 |
| 4,403,618 | 9/1983 | Turner et al. | 128/804 |
| 4,446,874 | 5/1984 | Vaguine | 128/804 |
| 4,462,412 | 7/1984 | Turner | 128/804 |
| 4,530,358 | 7/1985 | Forssmann | 128/328 |
| 4,586,516 | 5/1986 | Turner | 128/804 |
| 4,589,424 | 5/1986 | Vaguine | 128/804 |
| 4,601,296 | 7/1986 | Yerushalmi | 128/804 |

FOREIGN PATENT DOCUMENTS

| 0111386 | 6/1984 | European Pat. Off. . |
| 1440333 | 4/1969 | Fed. Rep. of Germany . |
| 2060923 | 7/1971 | Fed. Rep. of Germany . |
| 2648908 | 5/1978 | Fed. Rep. of Germany . |
| 0028338 | 3/1977 | Japan . |

OTHER PUBLICATIONS

NASA Tech Briefs, p. 59, Spring 1980.
"A Microwave System...", by Magin, IEEE Transactions Microwave Theory Technology, MTT-26, No. 8, pp. 546-549, Aug. 1978.
Article: "A Localized Current Field...", by Astrahan et al., Med. Phys. 9(3), pp. 419-424, May/Jun. 1982.
"Techniques... Hyperthermic... Carcinoma", by Robinson et al., IEEE Transactions Microwave Theory and Technology, MTT-27, No. 1, pp. 78-83, Jan. '79.
Book: Hyperthermia in Cancer Therapy -F. K. Storm.
The October 1976 Issue of Microwaves, Article Entitled: "Microwaves Score TKO in Fight Against Cancer".

Primary Examiner—Lee S. Cohen
Attorney, Agent, or Firm—Sandler & Greenblum

[57] ABSTRACT

This invention relates to a hyperthermia device for treating cancerous growth in a living body utilizing electromagnetic waves. It features an ability for maintaining the temperature of the heated region by effectively controlling the output of the electromagnetic waves and the temperature of the heated body surface accurately which was heretofore considered most difficult.

5 Claims, 35 Drawing Sheets

HYPERTHERMIA DEVICE

This application is a continuation of application Ser. No. 014,138 filed Feb. 12, 1987 (now abandoned) which, itself, is a continuation of application Ser. No. 707,490 filed Mar. 1, 1985 (now abandoned).

BACKGROUND OF THE INVENTION

1. Field of the Invention

This invention relates to a hyperthermia device and in particular to the hyperthermia device which deteriorates the regenerative functions of cancerous cells and thereby liquidating them by heating them with electromagnetic waves.

2. Description of the Prior Art

In recent years, hyperthermia has been given wide attention and papers have been written on hyperthermia which deteriorates the regenerative functions of cancerous cells and thereby liquidating significant portion of them by applying heat of approximately 43° C. for one or two hours and repeating the treatment at certain intervals. (F. K. Storm: Hyperthermia in Cancer Therapy, C. K. Hall Med.Pub., Boston (1983)).

There are two kinds of hyperthermia therapies: general heating and local heating methods. Three methods are proposed for the local heating: one utilizes electromagnetic waves and the second uses electric conduction and the third uses ultrasonic waves.

Researchers concluded that the optimum temperature for attacking cancerous cells is 43° C. or thereabouts. Temperatures below this will weaken the effects and temperatures above this will damage normal cells. Hyperthermia aims at liquidating cancerous cells without heating normal cells by maintaining the temperature in a confined narrow range.

However, it has been quite difficult by conventional means to keep the temperature of cancerous cell approximately at 43° C. for one or two hours due to the peculiar functions of a living body. Particularly heating by electromagnetic waves has been put aside for a long time because a significant portion of the electromagnetic waves is absorbed by the body surface thus the method unfit for heating the deep parts of a living body. Meanwhile, inventors have been active in the study of the effectiveness of hyperthermia therapy on cancerous growths at the deep parts of a living body using electromagnetic waves.

SUMMARY OF THE INVENTION

An object of this invention is to introduce a heating device for hyperthermia provided with functions for controlling the temperature of the heated region in a living body in a predetermined certain range for a certain time period utilizing electromagnetic waves.

A further object of this invention is to introduce a device that is capable of heating a predetermined region at a certain temperatures accurately for a long period of time by controlling the output of a microwave generating means or by controlling as necessary the capacity of the cooling fluid by activating the output controlling means or the cooling fluid controlling means of the main control means by detecting changes in temperatures of the heated regions.

DETAILED DESCRIPTION OF THE PREFERRED EMBODIMENT

(First Embodiment)

Description will hereafter be given of the first embodiment of the present invention with reference to FIGS. 1 through 7.

Figure 1:
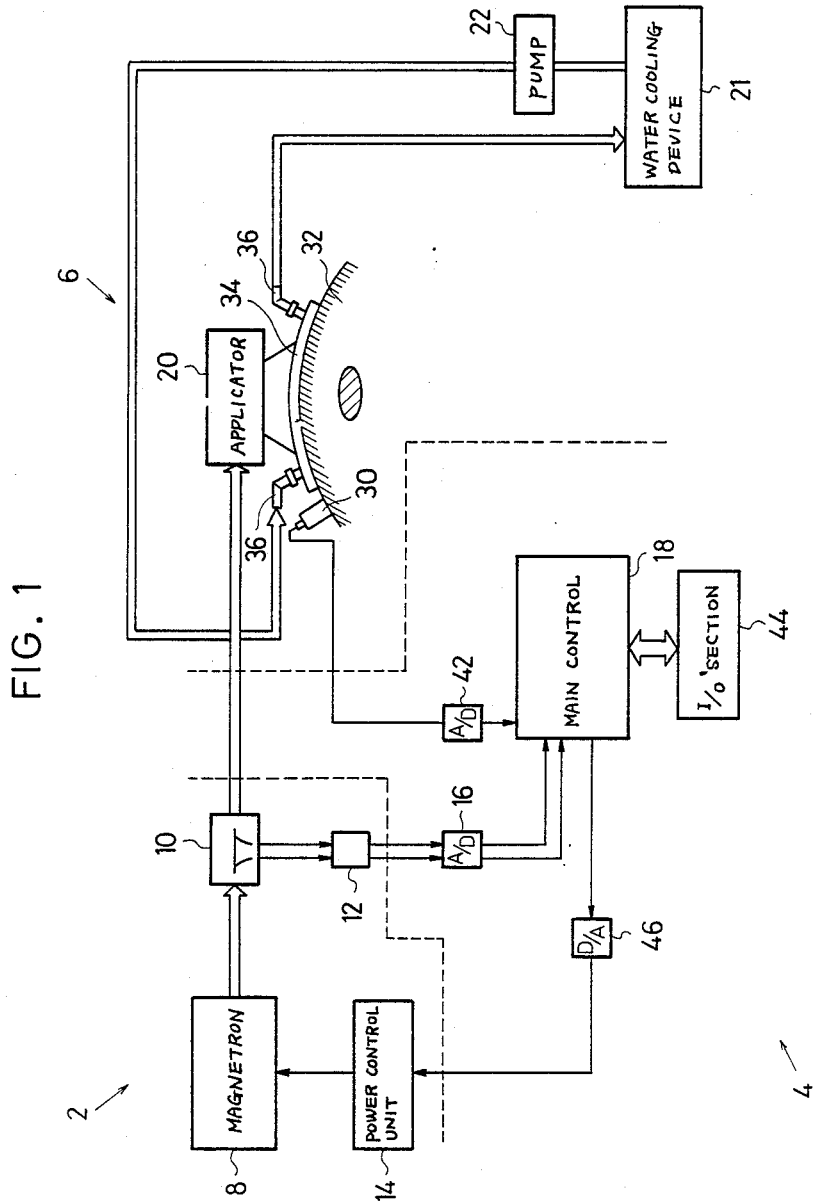
FIG. 1 shows the entire system of the first embodiment of the present invention.

FIG. 1 shows the entire diagram of the first embodiment. In this embodiment, the hyperthermia heating device comprises microwave generator 2 as an electromagnetic wave generating section and control 4 which includes the first through fourth controllers and microwave radiating section 6.

The microwave generator 2 comprises a magnetron 8 as an electromagnetic wave generator, a directional coupler 10 mounted on the output side of the magnetron 8, a diode 12 as the sensor which detects output level of the magnetron 8 via the directional coupler 10 and power control unit 14 which controls the output of the magnetron 8. The power control unit 14 is a control circuit which adjusts the output of the magnetron 8 by changing the anode voltage of the magnetron 8. The directional coupler 10 is a device which takes out incident waves and reflected waves separately and the electromagnetic waves thus taken out are detected by the diode 12 and, after voltage is converted, are fed to the main controller 18 via an analog-digital converter 16 (hereafter called A/D converter).

The main controller 18 subtracts the power level value of the reflected waves from the power level of the incident waves to calculate the power of the microwaves which is effectively fed to the applicator 20, which will be described later, and activates the first through fourth controlling means to control the output of the magnetron.

On the other hand, in this embodiment, the microwave radiator 6 comprises the applicator 20 which applies the microwaves to living body and the opening of the applicator 20 at which is mounted the cooling mechanism 34 for cooling the surface of living body and a temperature sensor 30 for detecting the temperature of cancerous cells.

Figure 2:
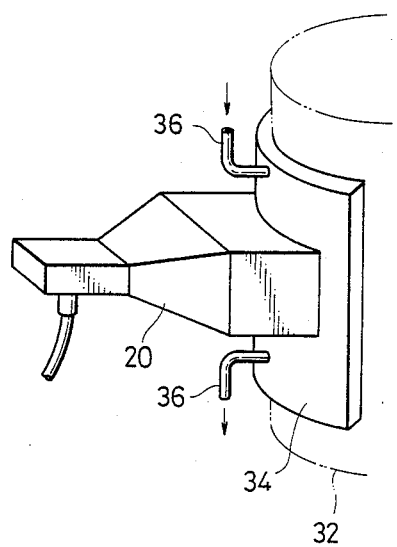
FIG. 2 is a perspective view showing an example of the applicator.

The applicator 20 comes into contact with a living body as shown in FIG. 2, and acts as an antenna which irradiates the living body 32 with microwaves to heat up cancerous cells. The cooling mechanism 34 is provided to prevent burns over the skin by heating due to dielectric loss at the contact on skin surface. The cooling mechanism 34 has pipes 36 for the cooling water which is cooled by the cooling device 21 and forced to circulate by a pump 22 and flows through the cooling mechanism 34 to cool the living body at the opening of the applicator 20.

The sensor 30 detects the temperature of cancerous cells and data obtained are used to make adjustment of the output of the magnetron 8 via the first through third control means of the main control 18.

The main control section 18 has a cooling fluid cooling means. According to the data from the sensors 12 and 30 via the A/D converters 16 and 42, and the data from the I/O section 44 and from the operator, the main control 18 controls the rotation frequency of the pump 22 and the output of the magnetron 8 via the D/A convertor circuit 46 to maintain the cancerous cells at desired temperatures and at the same time sends out various data as described above to the I/O section 44 to inform the operator of the heated condition.

Figure 3:
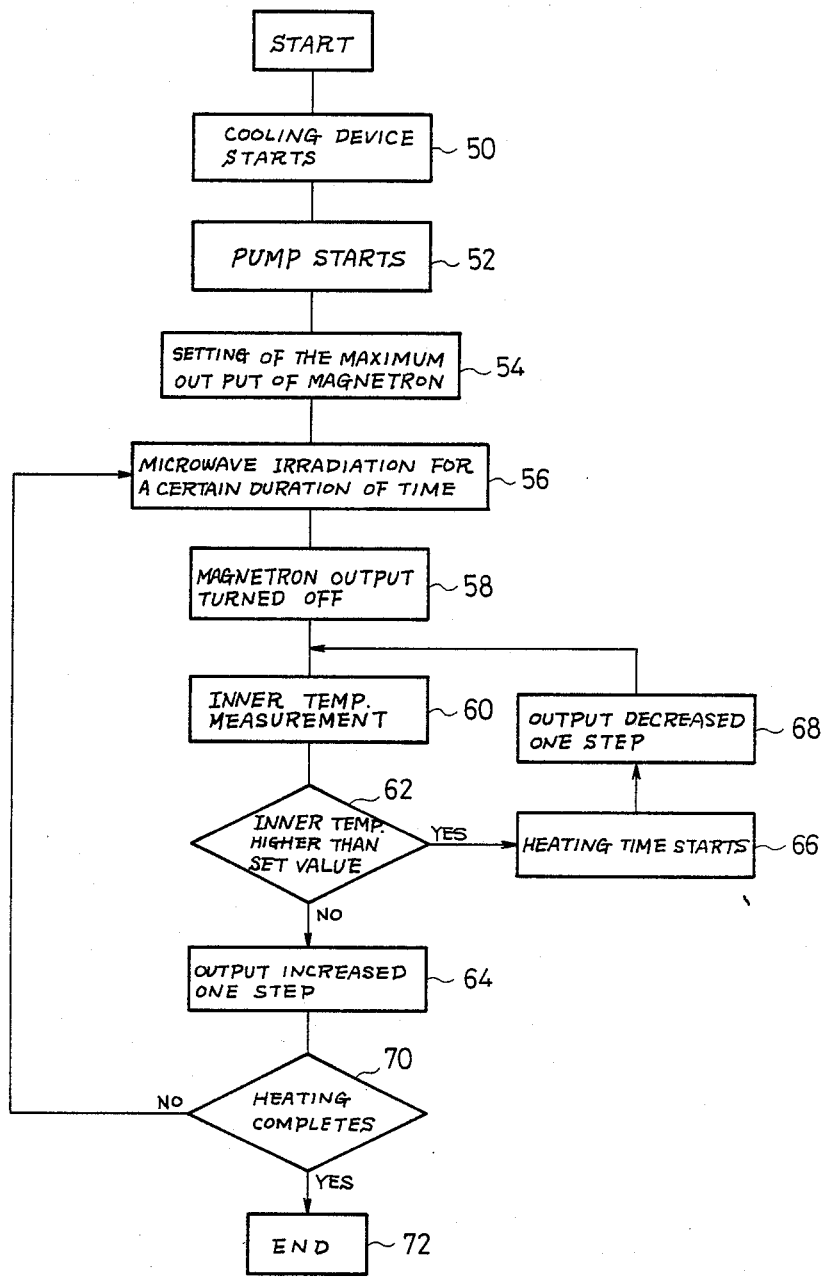
FIG. 3 is a flow chart illustrating the operation of the system shown in FIG. 1.

The entire operation of the device is described referring to the FIG. 3. Cancerous cells are heated to 43.5° C. In this first embodiment, the first control means decreases the output, the second control means interrupts the output, the third control means increases the output and the fourth control means controls the maximum level, and the cooling fluid cooling means functions to control the flow amount of the cooling fluid.

Figure 4:
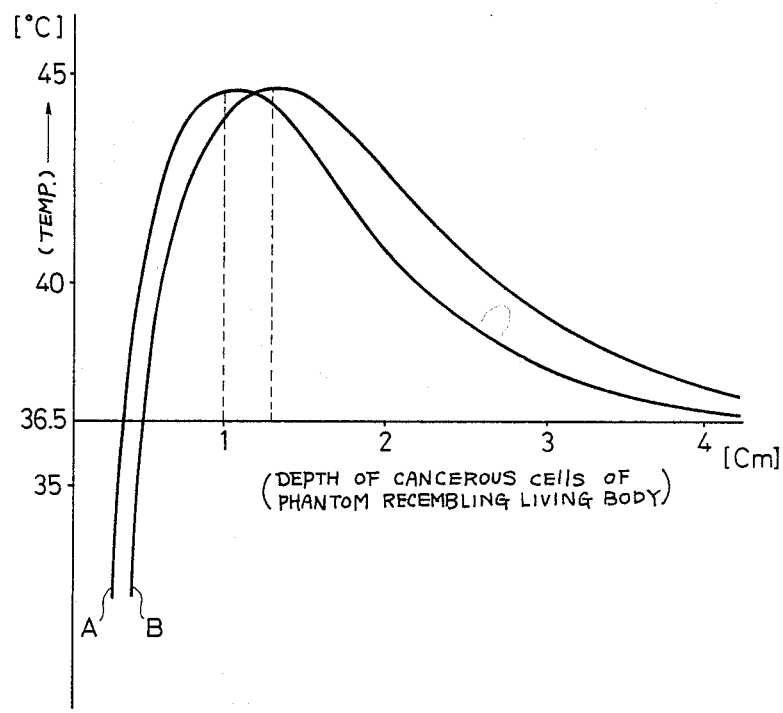
FIGS. 4 to 7 are diagrams showing actions and operations of the embodiment shown in FIG. 1.
Figure 5:
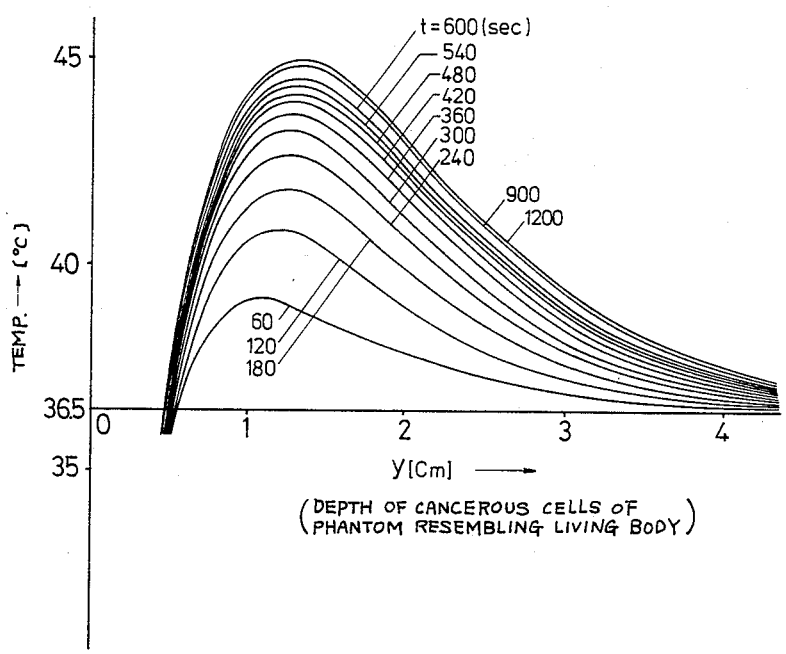

First, the cooling device 21 is activated by the cooling fluid control means of the main control 18 (refer to 50 in FIG. 3) to sufficiently cool the water and the rotation frequency of the pump 22 is controlled (refer to 52 in FIG. 3). Then the operator sets the I/O section 44 at the predetermined maximum output level of the magnetron 8 for the depth of cancerous growth (refer to 54 in FIG. 3). The reason for setting the maximum output of the magnetron for the depth of the cancerous growth is that if the microwave output is large, the peak of the temperature occurs near the surface and if it is small the heat peak penetrates deep into the cells. FIG. 4 shows results of the experiment using a phantom model resembling a living body, wherein temperature distribution (A) is obtained by radiating microwave of 2450 MHz at a standard value and is compared with the temperature distribution (B) by microwave radiation 3 dB less than the standard value. This frequency band is the highest used for heating therapy thus the heating depth is limited to the surface. Nevertheless, it is evident that the temperature peak of the distribution of output 3 dB less (B) reaches about 0.25 cm further. However, it takes more time to heat the cancerous cells to the predetermined temperature if the output is decreased. FIG. 5 shows an experimental result of temperature changes of the heated region at a certain time intervals and the curve represents the characteristic curve of this embodiment.

Setting of the maximum output of the magnetron 8 in operation is performed by the fourth control means in the main control 18, on the data from the directional coupler 10. In other words, the maximum output of the magnetron 8 is determined by obtaining the microwave output effectively fed to the applicator 20 which is the difference between the power values of the incident waves and reflected waves detected by the directional coupler 10, and by equalizing this output value and the value determined by the operator at the I/O section 44. In this the setting of the predetermined level may be made using a phantom model in advance.

After setting the output of the magnetron, irradiation is continued for a certain period of time (refer to 56 in FIG. 3) and the output of the magnetron is cut off (refer to 58 in FIG. 3) and temperature measurement begins (refer to 60 in FIG. 3).

This measurement is performed using the temperature sensor 30 which measures the temperature of cancerous cells. Microwave irradiation is cut off because the microwave causes errors in measurement by the temperature sensor 30. If a temperature sensor which is less susceptible to microwaves is used, cutoff of the magnetron output (refer to 58 in FIG. 3) will be unnecessary.

After the temperature measurement, the value is compared with the inner temperature value inputted by the operator (43.5° C.) to see if it is higher or lower (refer to 62 in FIG. 3).

If it is lower than the operator input value, the third control means inside the main control 18 functions immediately to give a command to the power control unit 14 to raise the output of the magnetron 8. However, the output value must not exceed the originally inputted maximum power (refer to 54 in FIG. 3). When the next irradiation time comes, irradiation starts at this value. The microwave irradiation is repeated until the temperature of cancerous cells exceeds the set value and the set value is raised step by step during the measurement to perform the next irradiation by a newly set value.

When the temperature of cancerous cells becomes higher than the set value the second control means in the main control 18 suspends the irradiation until temperature of cancerous cells becomes lower than the set value, and measurements are repeated. The whole control is performed by the main control 18. On the other hand, the output of the magnetron is decreased step by step by the first control means of the main control (refer to 68 in FIG. 3) to set up value for the next irradiation during measurement period.

The relation between heating time and liquidation of cancer is influenced by the duration of time after the temperature at the cancerous cells reaches 43° C. or thereabouts. In this example, heating time is measured from the time the cancerous cells exceeds the set value and heating is suspended when the heating time preset by the operator expires (refer to 72 in FIG. 3).

Figure 6:
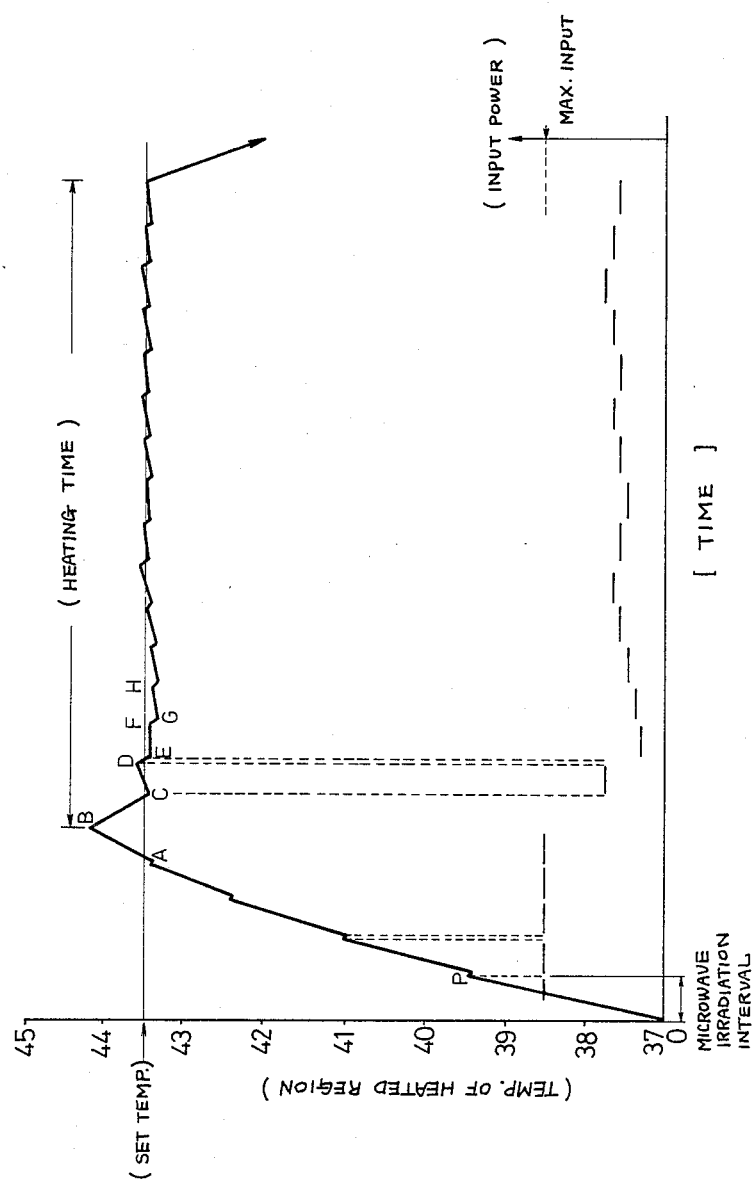

FIG. 6 shows the relation between the heated condition of cancerous cells and the output of the magnetron during each microwave irradiation and temperature measurement. In this drawing, the intervals in which the temperature distribution increases represents the time of microwave irradiation and the decrease of temperature distribution represents the measurement time. At the time of measurement the output of the magnetron is zero. The point B in the drawing is the time the measurement begins and the heating period starts when the inner temperature first exceeds the set value as a result of microwave irradiation by the maximum output of the magnetron. And measurement continues until the inner temperature becomes less than 43.5° C. (refer to B.C in FIG. 6) and during which time the first control means in the main control 18 lowers the output of the magnetron one step (refer to 68 in FIG. 3) to set microwave output for the next irradiation. The inclination of the line CD is less than the line AB. If the temperature at the subsequent irradiation does not reach 43.5° C. due to an excessive decrease of the output set value of the magnetron at the time of temperature measurement (e.g. EF in FIG. 6), the output is raised during the subsequent measurement period (e.g. FG in FIG. 6) as illustrated in the flow chart, 64 in FIG. 3 to raise the inclination again (e.g. GH in FIG. 6). By this repetition the temperature control with little ripples will be obtained.

It is necessary, during microwave irradiation, to set the maximum output of the magnetron and irradiation time to limit the rise of the temperature to less than 1.5° C. in excess of 43.5° C. at the time it first exceeds 43.5° C. This is because normal cells are adversely affected by temperatures exceeding 45° C. One possible method to determine the set value is to limit temperature increase during the first stage of the microwave irradiation (Refer to OP in FIG. 6) to 3° C. This in based on the fact that, as shown in FIG. 5, the temperature tends to go up during the first stage for each time period and the rate of temperature rise decreases by ½ in the vicinity of 43.5° C.

Figure 7:
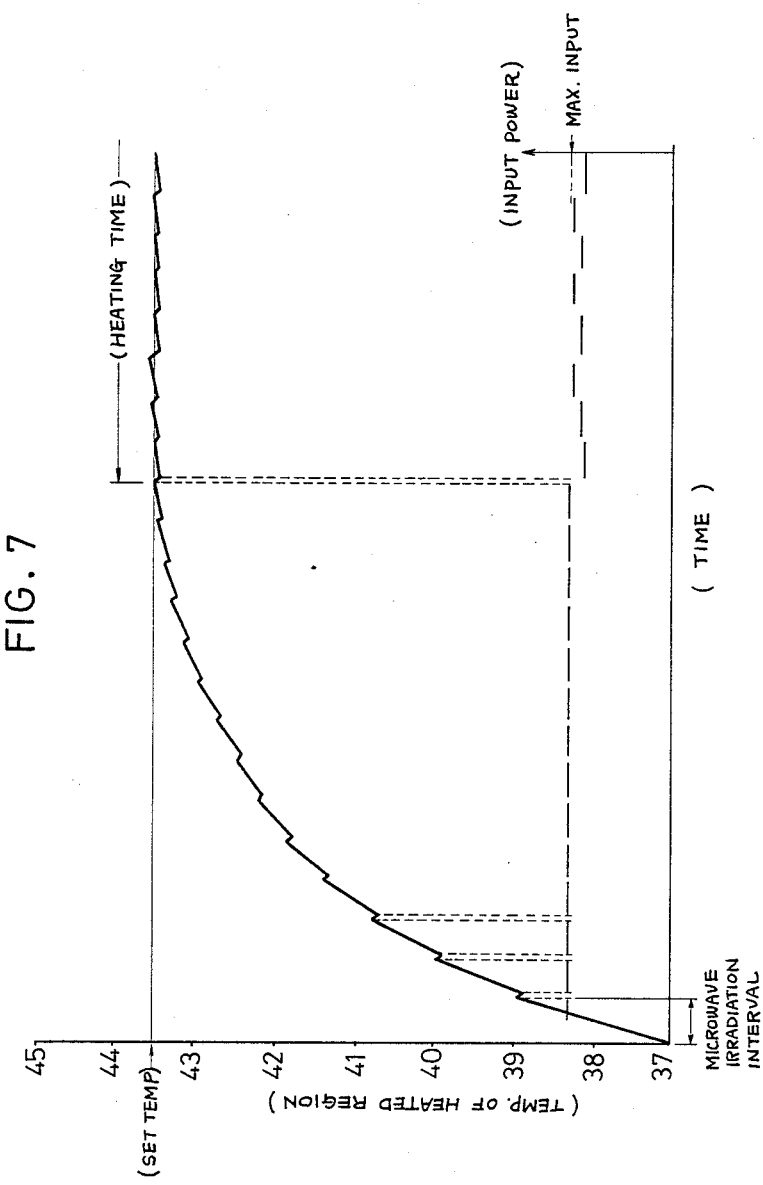

FIG. 7 shows the temperature of the cancerous cells with a lower output of the magnetron in comparison with FIG. 6 and the start of heating lags behind that of FIG. 6.

Since relatively low frequencies are used for heating deep regions, an oscillator and linear amplifier suitable for microwave of lower frequency may be used in place of the magnetron used in the above embodiment. In this case, change of power is done by changing the plate voltage of a linear amplifier or by changing power of an oscillator with thyristor control as in the case of controlling the magnetron. It will be necessary, however, to use an isolator to minimize the effect of reflected waves.

(Second Embodiment)

Figure 8:
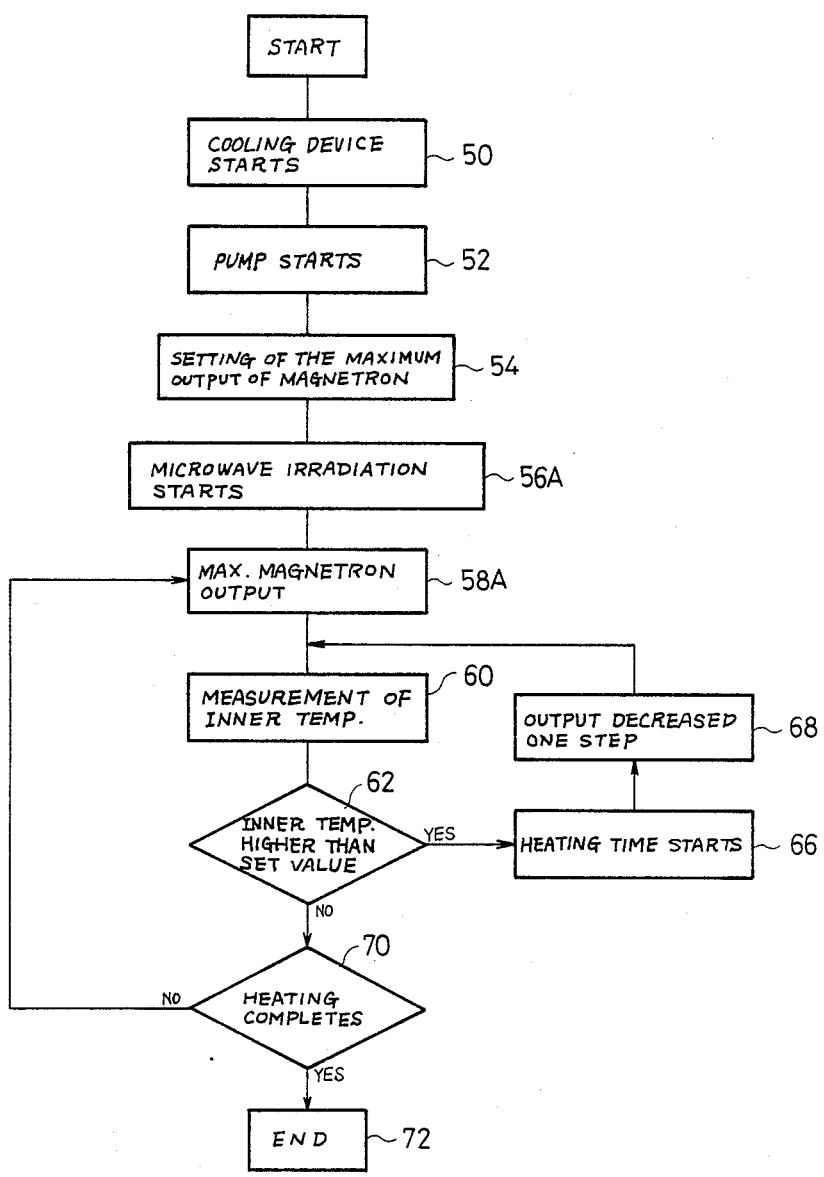
FIG. 8 is a flow chart illustrating the second embodiment.
Figure 9:
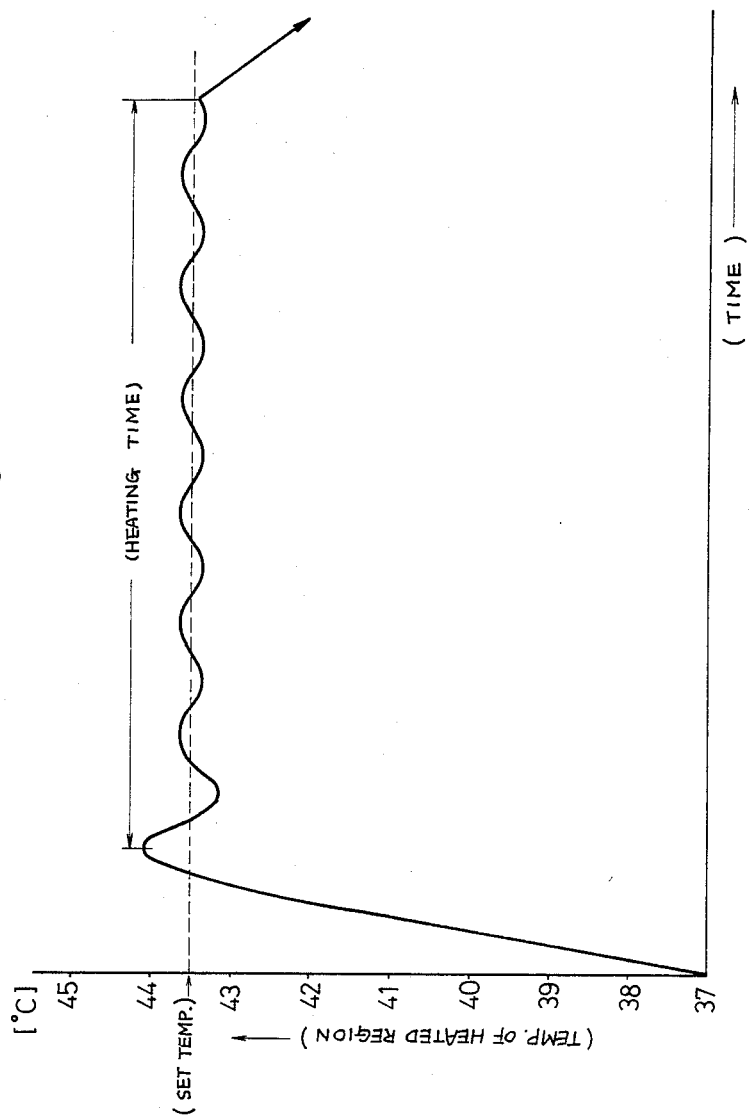
FIGS. 9 and 10 are diagrams showing the operation of the embodiment in FIG. 8.
Figure 10:
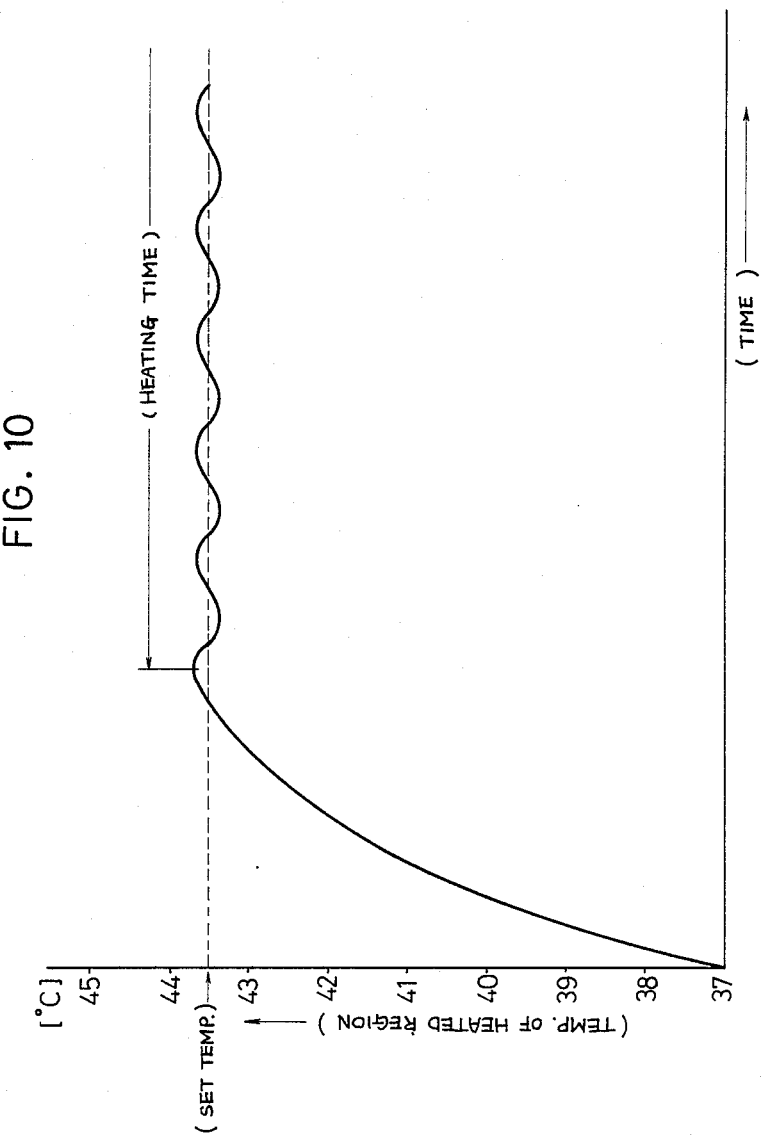

The second embodiment of the invention is described referring to FIGS. 8 through 10. FIG. 8 is a flow chart and FIGS. 9 and 10 are diagrams showing the tendency of temperature changes in heated regions.

While in the first embodiment the output of the magnetron 8 is shut off during temperature measurement of heated region of a living body 32, in the second embodiment, the magnetron 8 is kept in operation during the said temperature measurement to continuously output electromagnetic wave of a certain level. In this case, a thermometer (not shown) provided inside the living body 32 must be minutely constructed to avoid effects of the microwaves.

In this embodiment, the output of the magnetron 8 is increased to the maximum as soon as the temperature of heated region of the living body 32 becomes less than the preset value (refer to 58A in FIG. 8). This process simplifies the entire control, vastly different from the case of the first embodiment in which the output of the magnetron is raised by one step (refer to 64 in FIG. 3). The remainder of the configuration of this embodiment is the same as that of the first embodiment.

Because of this, in the second embodiment, as shown in FIG. 9, it becomes possible to raise the temperature of heated region of a living body continuously and rapidly providing relatively smooth control for optimum temperatures. Although there are some noticeable ripples, the general tendency of the temperature changes is acceptable. It also has an advantage of reaching the preset temperature of 43.5° C. in a relatively short time because the output of the magnetron 8 is operated continuously. FIG. 10 shows the temperature changes of the heated region when the output of the magnetron is decreased.

(Third Embodiment)

Figure 11:
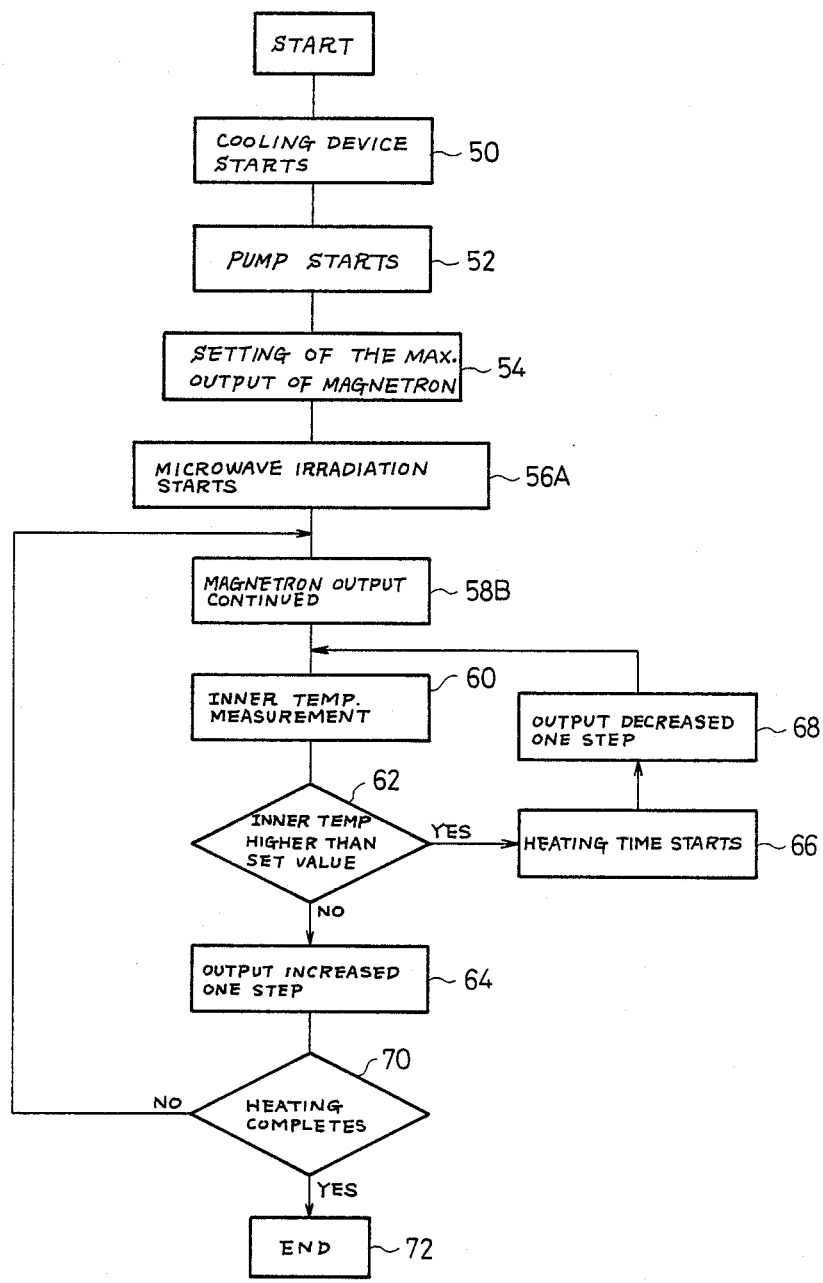
FIG. 11 is a flow chart of the third embodiment.
Figure 13:
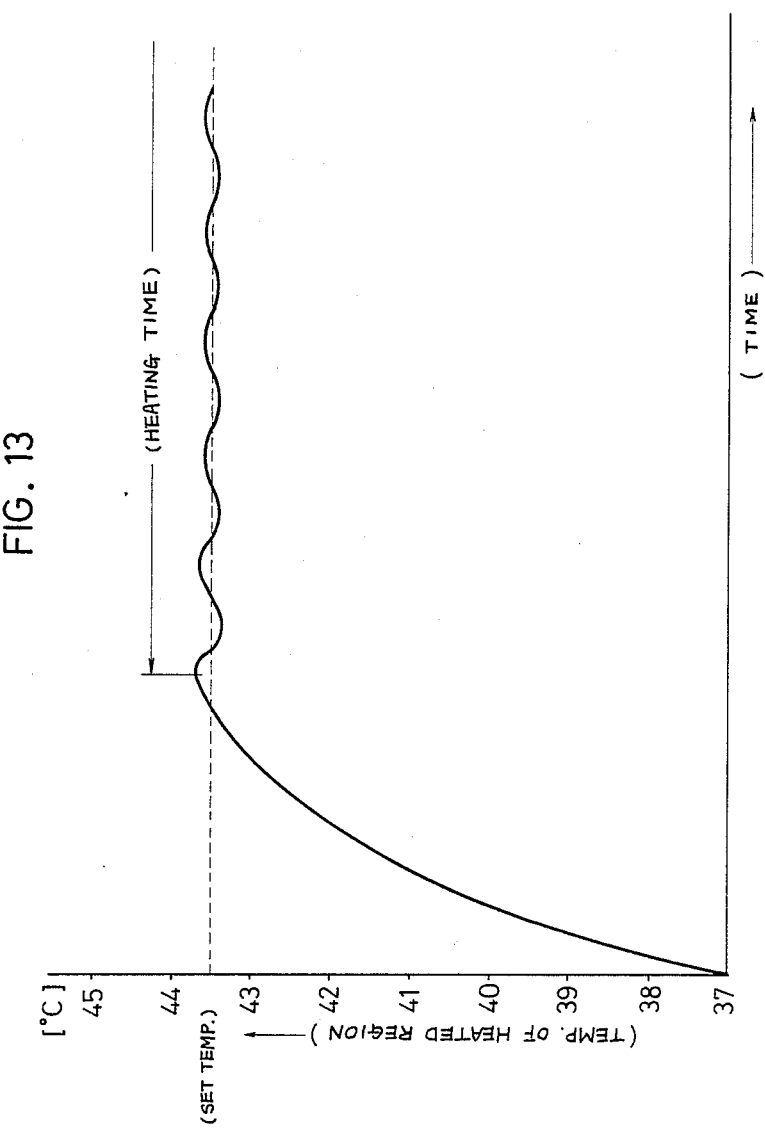

The third embodiment is described referring to FIGS. 11 and 13.

In the third embodiment, similar to the second embodiment, temperature changes of heated regions in a living body 32 is measured while electromagnetic waves are continuously radiated. It has configurational features as follows:

(1) After the maximum output of the magnetron 8 is set (refer to 54 in FIG. 11), the irradiation of microwaves is started (refer to 56A in FIG. 11) and the output is kept on during measurement of the heated regions.

(2) The output of magnetron 8 is raised and lowered as required in the same manner as described in the first embodiment.

The remainder of the configuration of this embodiment is the same as that of the first embodiment.

Figure 12:
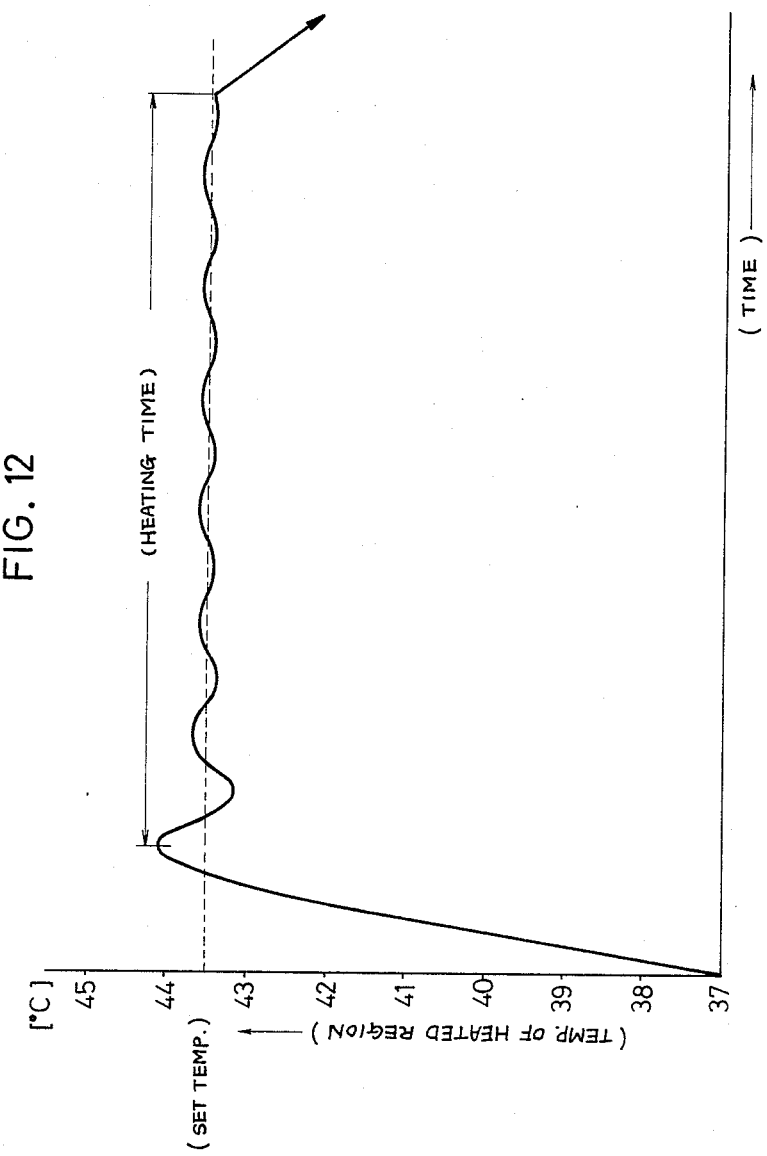
FIGS. 12 and 13 are diagrams showing the operation of the embodiment in FIG. 11.

This method has an advantage for producing less ripples of the heating temperature due to minute control of the magnetron output as required, in addition to continuous heating of the heated regions during temperature measurement (see FIG. 12). FIG. 13 shows the temperature change characteristic curve during heating period when the magnetron output is lowered in the third embodiment.

Although examples are shown where the entire device is operated with the maximum output of the magnetron in the first through third embodiment, the present invention is not limited to this method. The "setting of the maximum output of the magnetron" (refer to 54 in FIG. 13) in FIGS. 8 and 11 may be deleted, if necessary.

(Fourth Embodiment)

Figure 14:
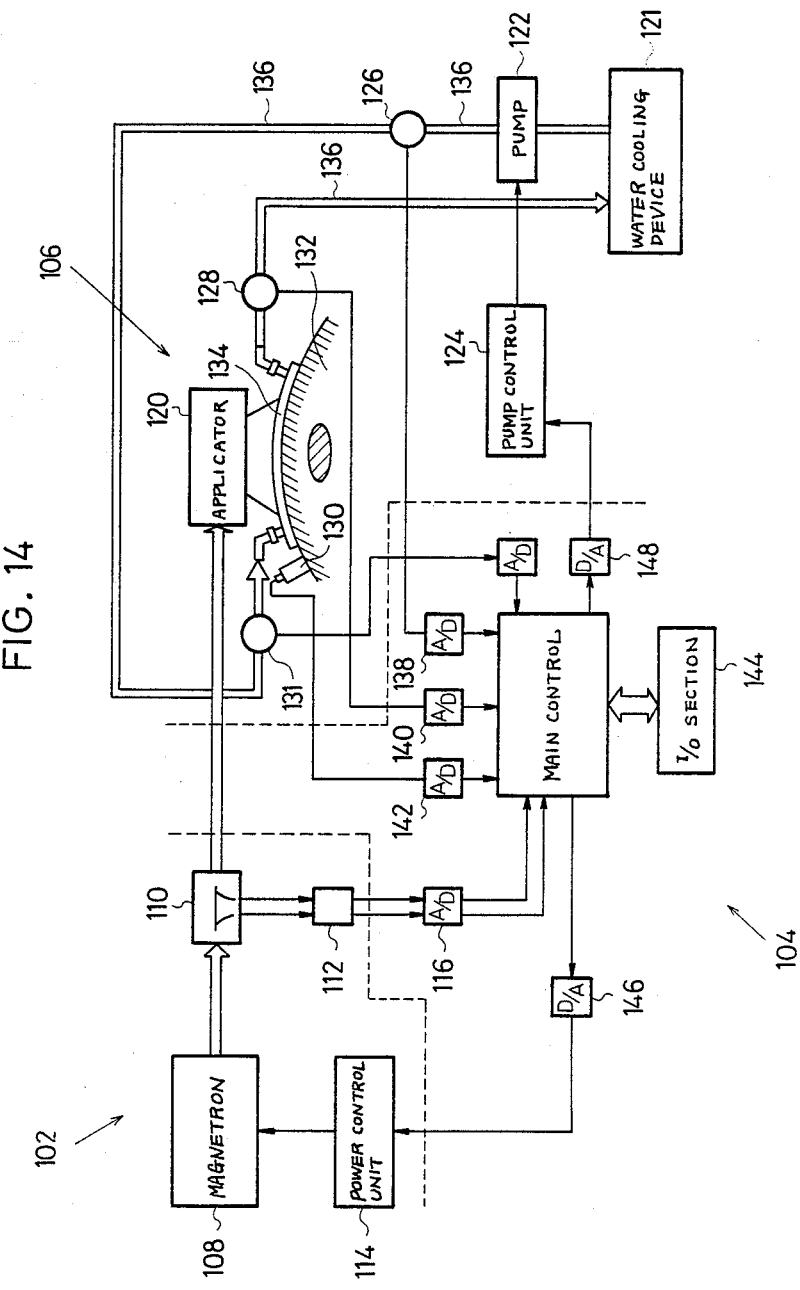
FIG. 14 shows the entire system of the fourth embodiment.
Figure 15:
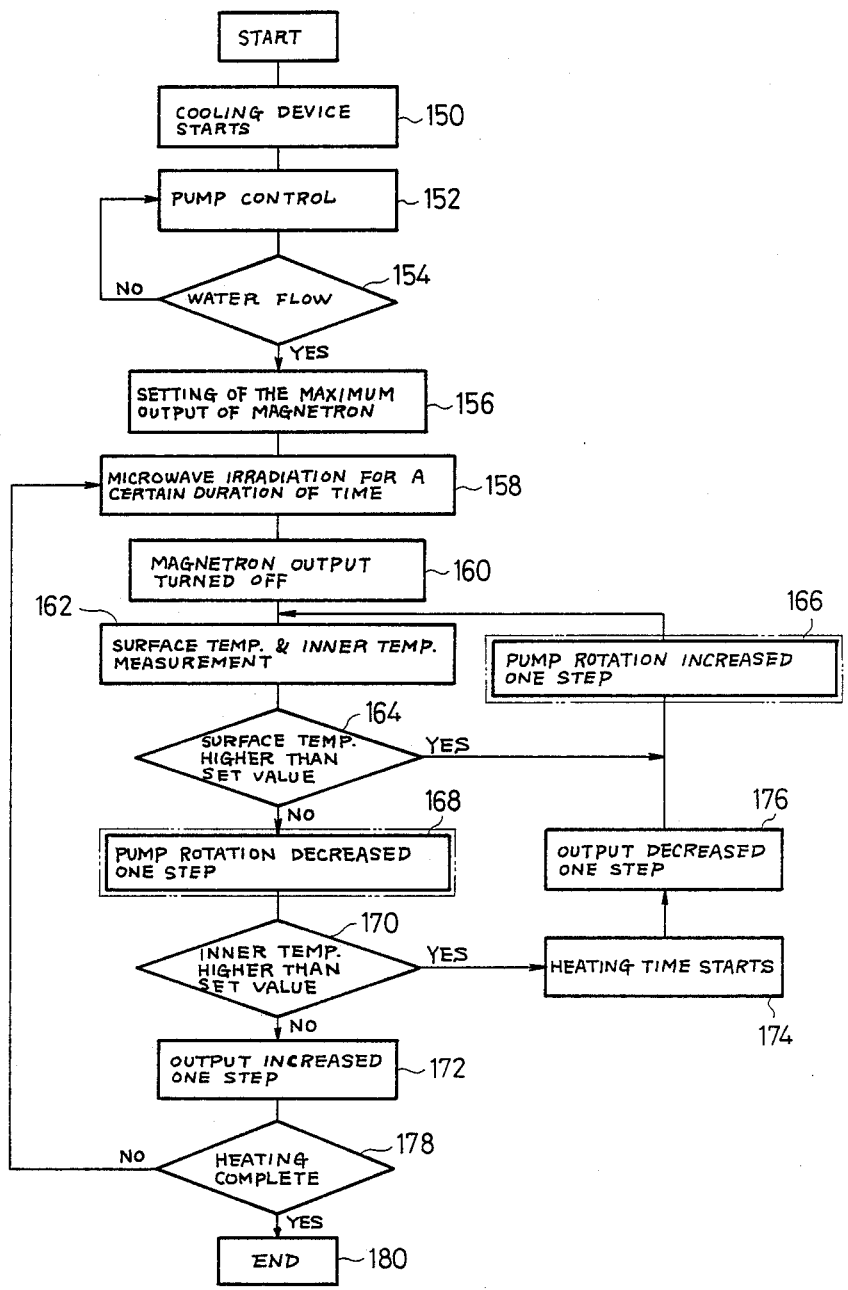
FIG. 15 is a flow chart showing the operation example in FIG. 14.

The fourth embodiment is shown in FIGS. 14 and 15.

In FIG. 14, the reference numeral 102 shows the microwave generating section as the electromagnetic wave generator, 104 the main control section which includes the first through third control of the output level similar to the first embodiment and the fourth control means which sets up the maximum output level and the cooling fluid control means. The reference numeral 106 shows the microwave radiating section.

The microwave generating section 102 comprises the magnetron 108 which is an electromagnetic wave generator, a directional coupler 110 and diode 112 and power control unit 114. The configuration is the same as that of the first embodiment.

The microwave radiating section 106 comprises in this embodiment an applicator 120 which irradiates a living body with microwaves and the opening of the applicator 120 at which is mounted the cooling section 134 which cools the surface of a living body and further comprises a flow sensor 126 which detects amount of cooling water flow in the cooling section 134, a temperature sensor 128 which detects the temperature of the water, and the temperature sensor 130 which detects the temperature of cancerous cells. The reference numeral 121 shows the cooling device which cools the cooling fluid, 122 a pump which causes the water cooled by the cooling device to circulate, and 124 a pump controller unit which controls the operation of the pump. This pump controller unit 124 is operated by commands from the cooling fluid controlling means in the main control 118.

The applicator 120 is constructed as that of the first embodiment and contacts the living body 132 as shown in FIG. 14 to irradiate the predetermined region in a living body 132 with electric waves, and as in the case of the first embodiment the cooling mechanism 134 is provided to prevent burns over the skin of the living body 132 that is exposed to the irradiation due to dielectric loss. The cooling mechanism 134 is provided with pipes 136 in which the cooling water flows and the water is caused to circulated through the pipes by means of the pump 136 to cool the opening of the applicator 20 which is the surface of the living body.

The rotation frequency of the pump 122 is controlled by a pump controller unit 124 and this rotation changes the amount of the water flow in the cooling mechanism 134 of the applicator 120 to control the temperature of the surface of the living body. The flowing amount of the cooling water is detected by the flow sensor 126 and the data thus detected are sent to the main control 118 via an A/D converter 138 which serves as a reference value for controlling the rotation frequency of the pump. Temperature sensor 128 which detects the temperature of the water of the cooling mechanism 134, is provided at the exhaust side of the cooling mechanism 134 and the data obtained by the sensor are used to calculate the temperature of the surface of the living body which contacts the applicator 120. This surface temperature serves as main information for controlling rotation frequency of the pump 122.

The internal temperature sensor 130 detects the temperature of cancerous cells information of which is used by the first through fourth control means of the main control 118 to control the output of the magnetron 108.

The main control 118, in the same manner as in the first embodiment, receives information from the sensors 128, 130 via the A/D converters 116, 142, information from the input section 144 which receives commands from the operator control the rotation frequency of the pump 122, and the output of the magnetron 108 through the D/A converters 146, 148 to maintain the temperatures of the cancerous cells and the body surface at the predetermined value and at the same time, main control 118 sends all of this information to the output section 144 to inform the operator of the heated condition.

The overall operation of the above device is described referring to FIG. 15. The temperature of the body surface that contacts the applicator is assumed to be 20° C. and the cancerous cells are to be heated to 43.5° C. In the fourth embodiment as in the above described first embodiment, the first control means decreases the output, the second control means interrupts the output, the third control means increases the output and the fourth control means controls the maximum level, and the cooling fluid controlling means functions to control the flow amount of cooling fluid.

First, the cooling device 121 is activated (refer to 150 in FIG. 15) to sufficiently cool the water and the frequency of the pump 22 is controlled by the cooling fluid control means of the main control to maintain the minimum circulation of the cooling water by the information from the flow amount sensor 126 (refer to 152, 154 in FIG. 15). Subsequently, as in the case of the first embodiment, the operator determines in advance the maximum output level of the magnetron 108 for the I/0 section 44 in accordance with the position of cancerous cells (refer to 156 in FIG. 15).

On the other hand, setting of the maximum output of the magnetron 108 in operation is from the directional coupler 110 as in the case of the first embodiment. After the set up of the magnetron 108 maximum output, irradiation is performed for a certain duration of time (refer to 158 in FIG. 15) and the output is shut off (refer to 160 in FIG. 15) and temperature measurement follows (refer to 162 in FIG. 15).

This temperature measurement, contrary to the first embodiment, is performed by the temperature sensor 128 for the body surface and the temperature sensor 130 for the cancerous cells. After the measurement, it is determined whether the body surface temperature is higher or lower than the surface temperature set up by the operator (20° C.) (refer to 164 in FIG. 15). If it is higher than the set value the cooling fluid control means of the main control 118 immediately gives a command to the pump controller unit to raise the frequency of the pump a step at a time until the surface temperature comes down below the set value by increasing the amount of water flow (refer to 166 in FIG. 15). When the surface temperature becomes lower than the set value the frequency of the pump is lowered by one step (not less than the minimum circulation) (refer to 168 in FIG. 15) to prevent the surface temperature from becoming too low. Now the internal temperature control begins (refer to 170 FIG. 15).

If the internal temperature is lower than the internal value set by the operator (43.5° C.), the main control 118 give a command via the third control means to the power control unit 114 to raise the set value of the output of the magnetron 108. Output value, however, does not exceed the originally set maximum value (refer to 172 in FIG. 15) because of the fourth control means of the main control 118. And the subsequent microwave irradiation is performed with the newly set value. In other words, irradiation and measurement are alternately repeated until the temperature of cancerous cells become higher than the set value and the set value of the magnetron 108 output is raised one step at a time utilizing the interval for measurement and the subsequent irradiation is performed with the newly set value.

When the temperature of cancerous cells exceeds the set value as a result of the above, the irradiation is suspended until the temperature of cancerous cells comes down below the set value and temperature measurement loop is repeated. This control is performed by the main control 118. On the other hand, during the measurement the output of the magnetron is lowered step by step (refer to 176 in FIG. 15) for subsequent irradiation. The rotation frequency of the pump is raised one step after the output of the magnetron is lowered one step in order to compensate for the decreased frequency of the pump as shown by the reference numeral 168 in FIG. 15. In other words, it s necessary to cool off the surface temperatures as soon as the temperature of cancerous cells exceeds the set temperature.

Now, the relationship between heating time and liquidation of cancerous cells depends on the time it takes for the temperature of cancerous cells to come near 43° C. Therefore, in this embodiment, the heating time is measured from the time the temperature of cancerous cells exceeds the set value and the heating is completed when the heating time set by the operator expires (refer to 180 in FIG. 15).

Figure 16:
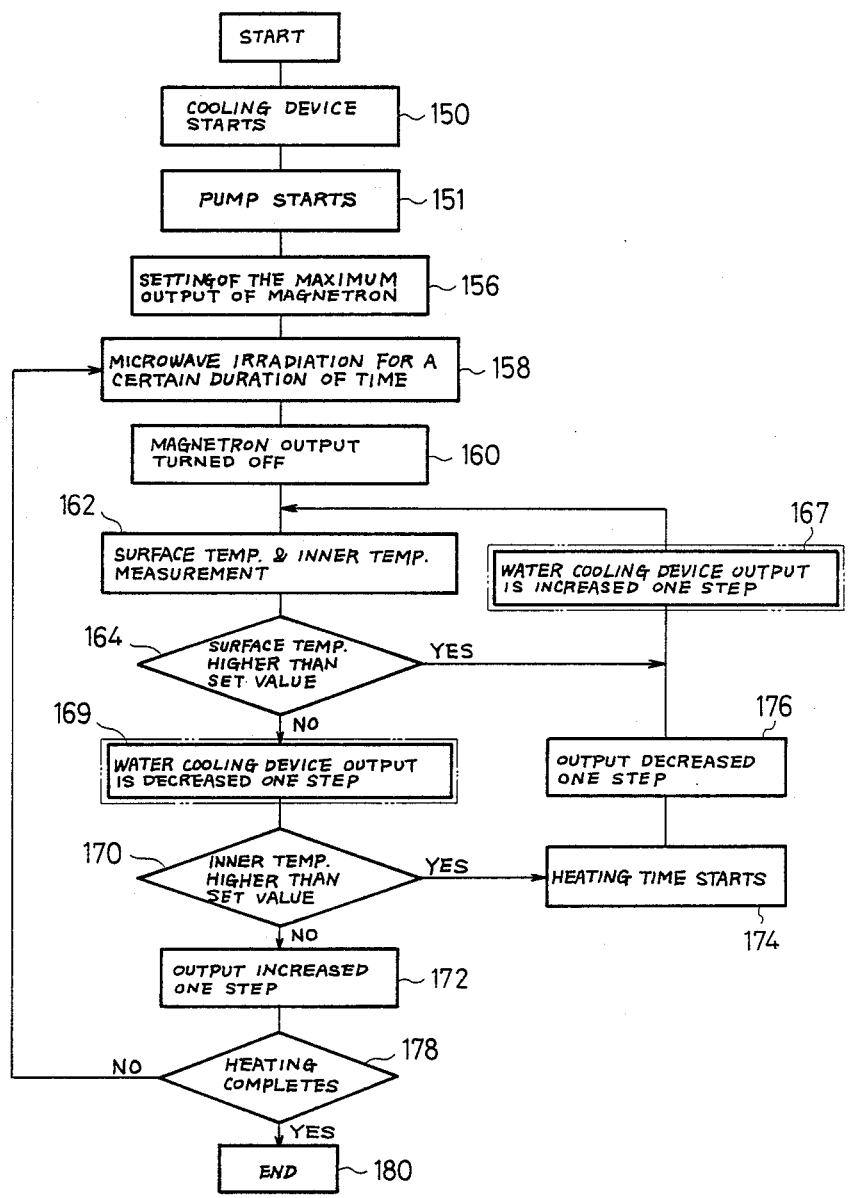
FIG. 16 is a flow chart showing a variation of the fourth embodiment.

Instead of controlling the flow of the cooling water to cool the body surface as in the fourth embodiment, the output of the cooling device 121 may be controlled by the cooling control means of the main control 118 by providing a cooling control circuit for the output control on the device (refer to 121 in FIG. 14) that cools the cooling water (refer to 167, 169 in FIG. 16).

In this case, the cooling fluid controlling means of the main control 118 functions as the control means of the temperature of the cooling fluid.

The fourth embodiment has an advantage that it effectively treats the specific region inside the body without excessively heating the body surface since temperature measurement is performed for surface of the body and inside the body separately. If the heated region is excessively heated, the cooling device 121 functions immediately to decrease the temperature, making the repetition time shorter than the characteristic curve of the temperature change in the case of the first embodiment, effectively preventing temperature rise of the body surface to perform hyperthermia therapy without giving patients undue pain.

(Fifth Embodiment)

Figure 17:
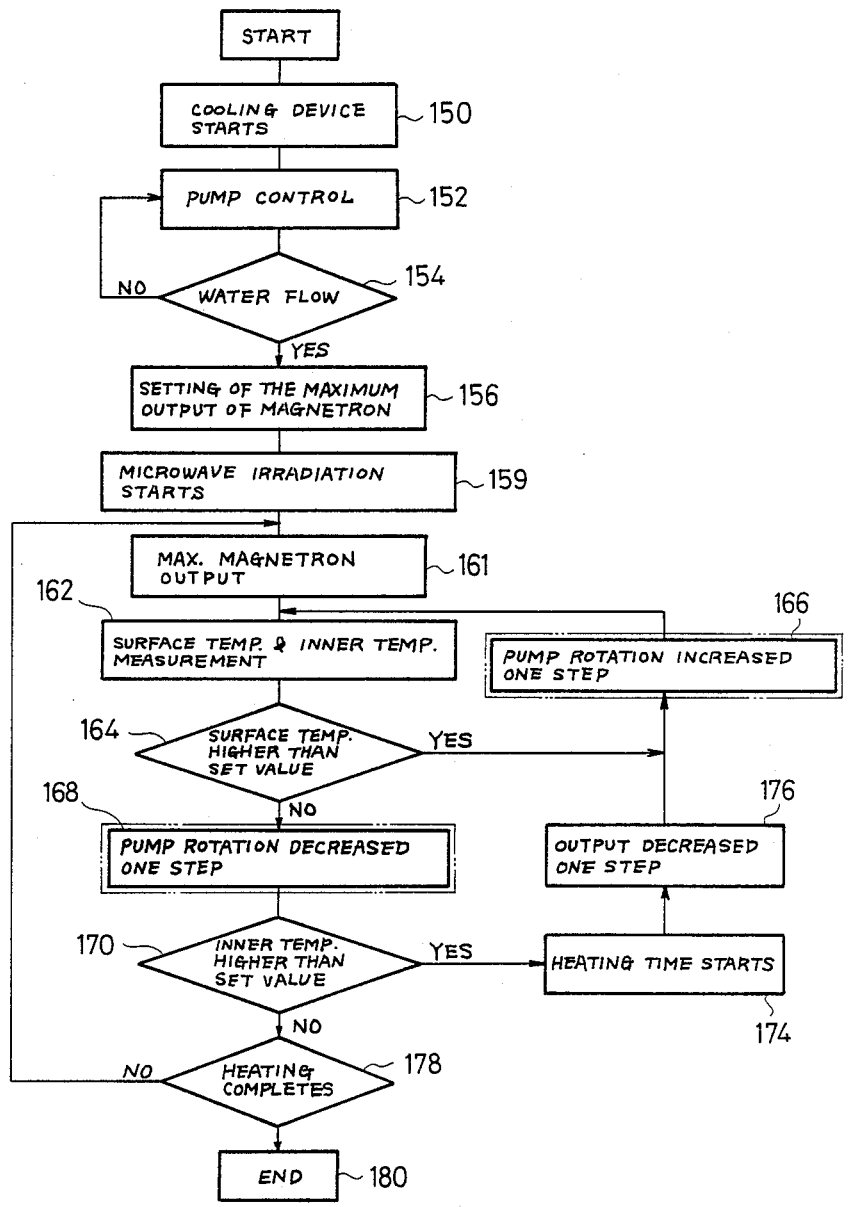
FIG. 17 is a flow chart showing the fifth embodiment.

FIG. 17 shows the fifth embodiment. While in the fourth embodiment, the output of the magnetron 108 is shut off when measuring the temperature of the heated region inside the body 132, in the fifth embodiment the magnetron 108 is activated continuously to generate electromagnetic waves of a predetermined level during the temperature measurement. In this case, the thermometer (not shown) provided inside the body must be of minute construction to avoid the effects of microwaves as in the case of the second embodiment.

In this fifth embodiment, when the temperature of the heated region becomes lower than the set value, the output of the magnetron 108 is immediately raised to maximum (refer to 161 in FIG. 17). Thus making the whole controlling very simple compared to the method used in the fourth embodiment in which the output of the magnetron is raised step by step. The remainder of the configuration of this embodiment is the same as that of the fourth embodiment.

In this embodiment, the heating characteristics exhibit a tendency similar to the second embodiment and the repetition time of whole changes is shortened compare to the case of the second embodiment, due to the operation of the cooling mechanism. This enables a speedy hyperthermia treatment as in the case of the fourth embodiment and the whole controlling system is made simple since intermittent control of the magnetron is unnecessary.

Figure 18:
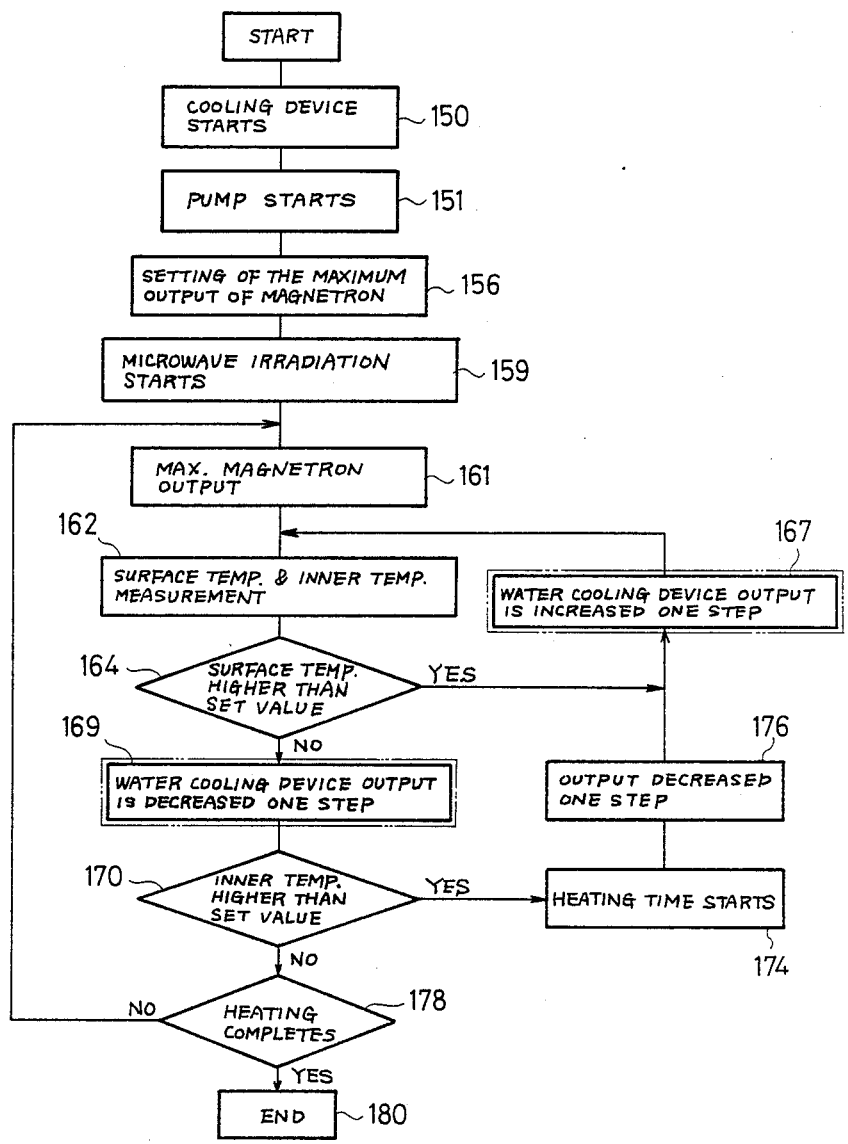
FIG. 18 is a flow chart showing a variation of the fifth embodiment.

Instead of controlling the output of the cooling pump, the output of cooling device may be controlled to change the temperature of the cooling water (refer to 164, 166 in FIG. 18).

(Sixth Embodiment)

Figure 19:
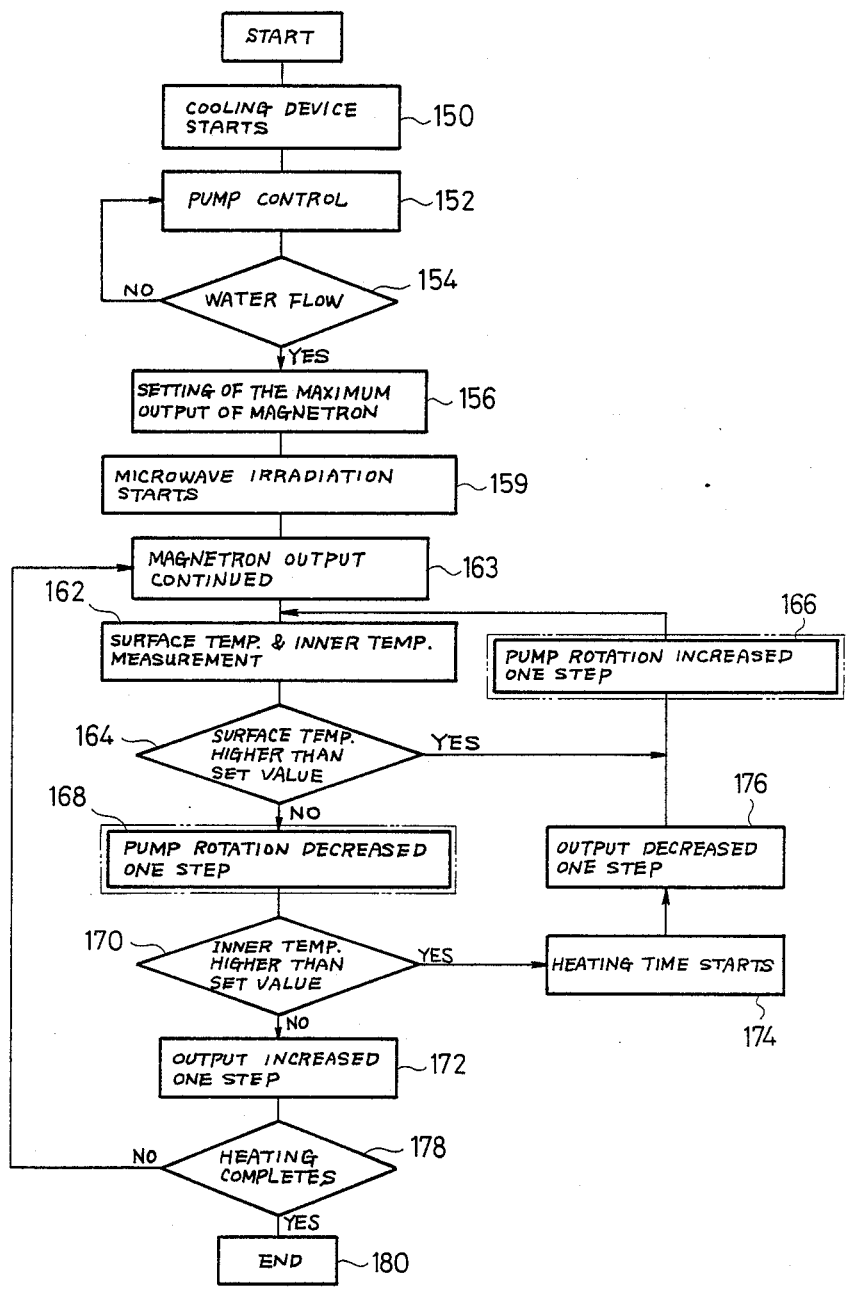
FIG. 19 is a flow chart showing the sixth embodiment.

FIG. 19 shows the sixth embodiment. In this embodiment, as in the fifth embodiment, the temperature changes in the heated region of the body is measured with continuous irradiation of electromagnetic waves to set the heated region at the preset value. It has the following configurational features:

(1) After setting the maximum output of the magnetron (refer to 156 in FIG. 19) the irradiation of microwaves is started (refer to 159 in FIG. 19) and the measurement of the temperature of the heated region is made while operating the magnetron continuously.

(2) The output of the microwave is increased one step at a time as necessary (refer to 172 in FIG. 19). The remainder of the configuration of this embodiment is the same as that of the fourth embodiment.

Figure 20:
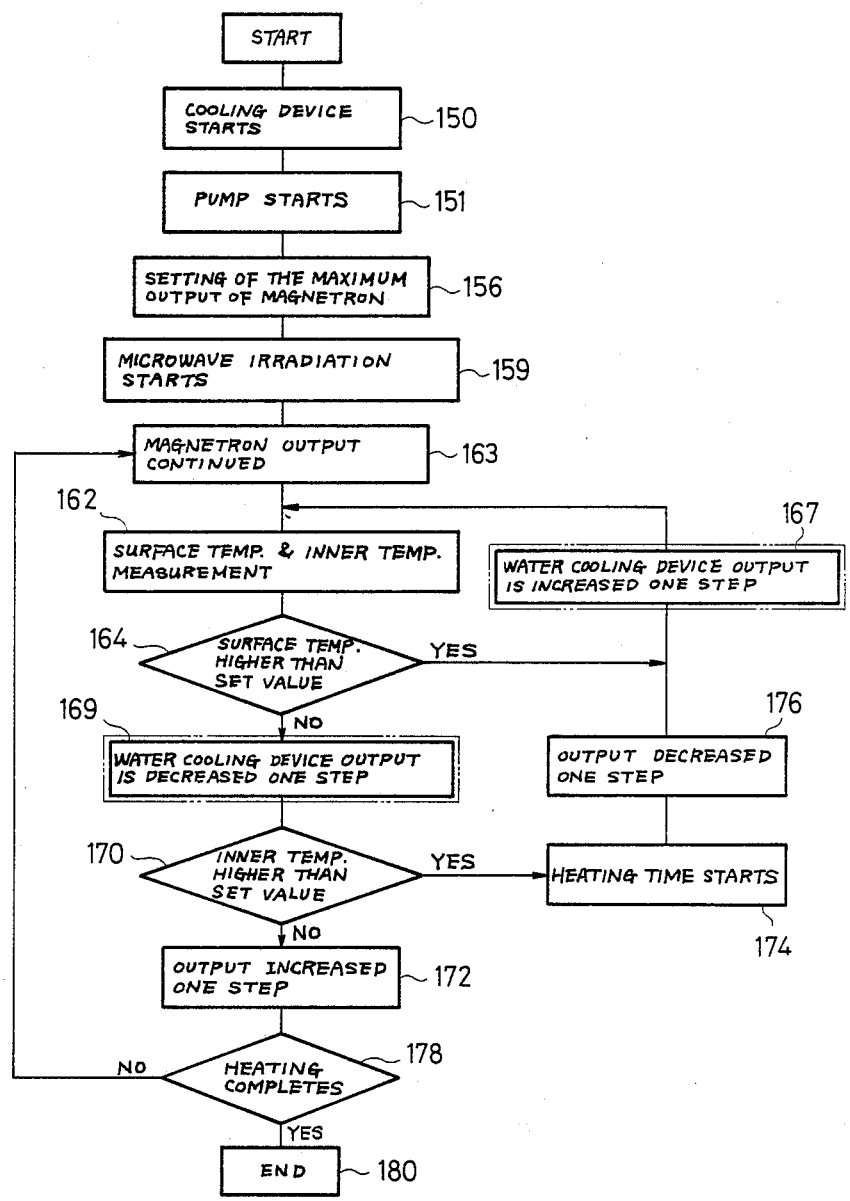
FIG. 20 is a flow chart showing a variation of the sixth embodiment.

As in the case of the fifth embodiment, the sixth embodiment, shown in FIG 20, performs a speedy treatment smoothly minimizing ripples in the temperature of the heated region.

Also in this embodiment, the output control of the cooling pump may be replaced by the control of the output of the cooling device to change the temperature of the cooling water (refer to 167, 169 in FIG. 20).

(Seventh Embodiment)

Figure 21:
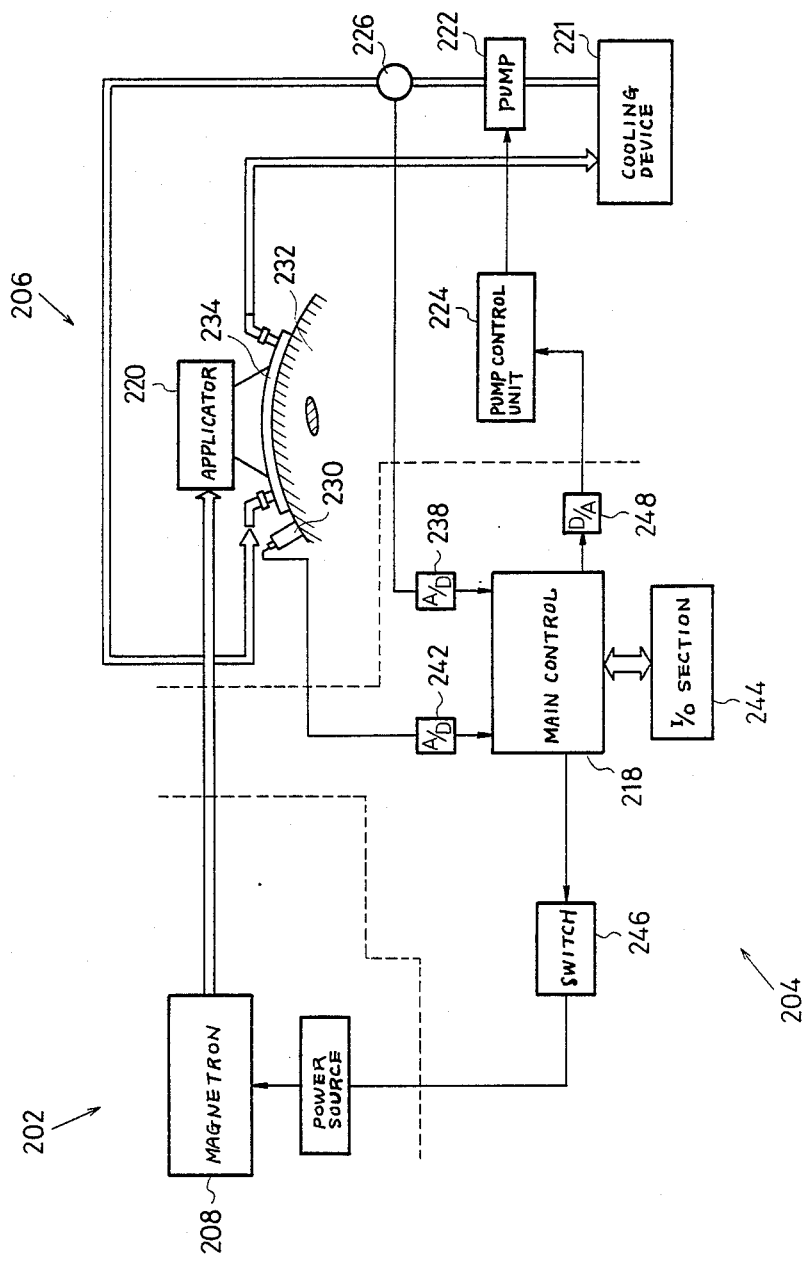
FIG. 21 is the entire system showing the seventh embodiment of the present invention.
Figure 22:
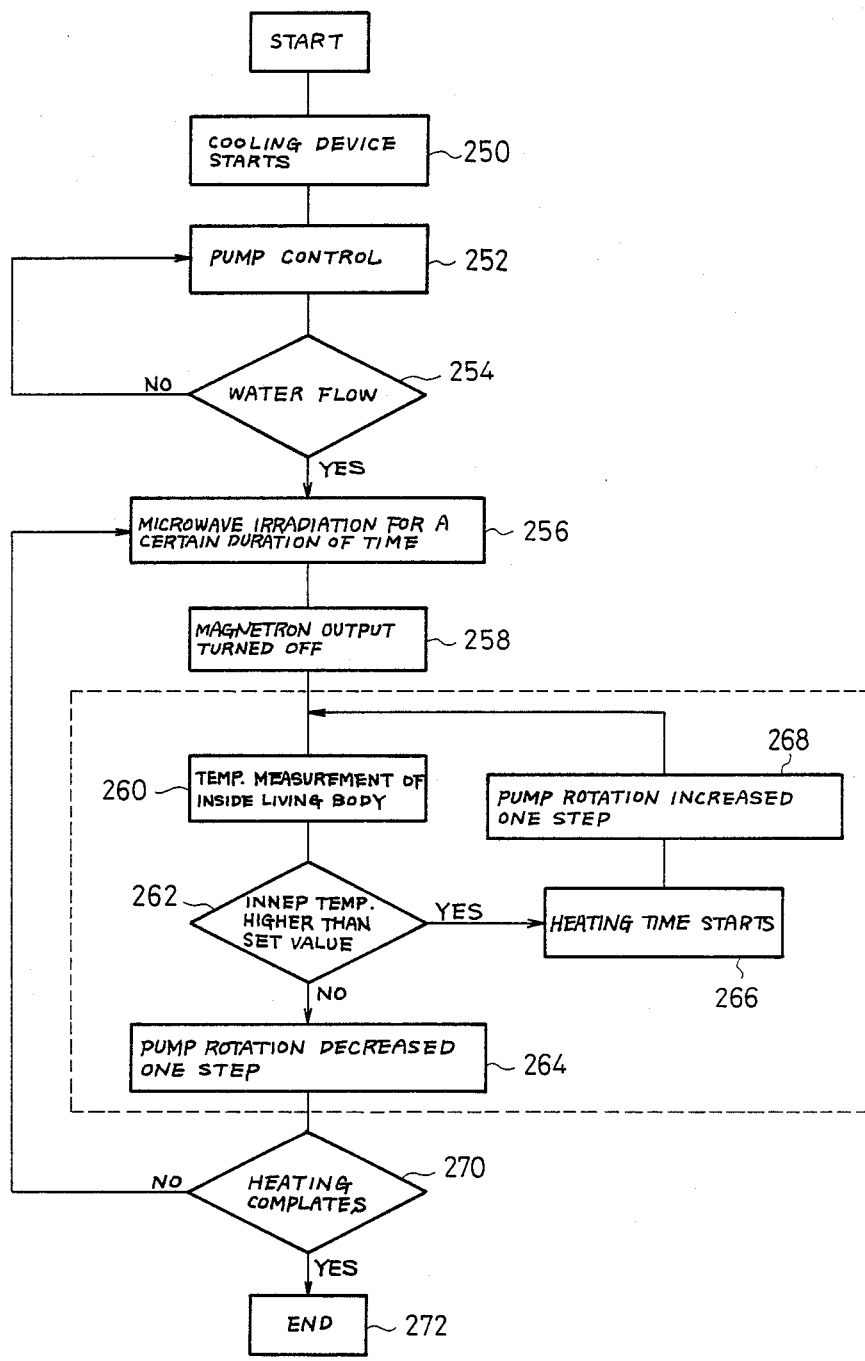
FIG. 22 is a flow chart of the operation in FIG. 21.
Figure 23:
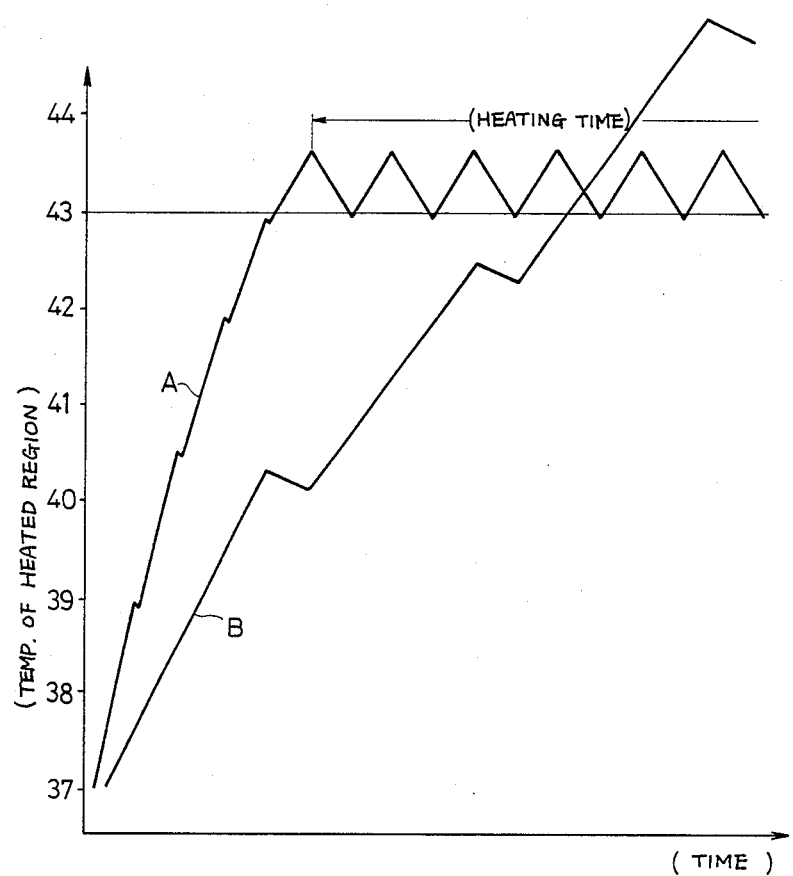
FIG. 23 is a diagram showing heated state of the embodiment shown in FIG. 21 as compared to conventional ones.

FIGS. 21 through 23 show the seventh embodiment.

In this embodiment, the output of the microwave generator (refer to 202 in FIG. 21) is set at a constant level to facilitate hyperthermia treatment on a living body while cooling the body 232 surface.

In the fundamental configuration, as shown in FIG. 21, this seventh embodiment does not have the temperature sensor 128 provided at the outlet side of the applicator 120 and its A/D converter 140 and the temperature sensor 131 provided at the inlet side of the applicator 120 and its A/D converter as in the case of the fourth example (see FIG. 14).

The functions and operation of the seventh embodiment are described referring to FIG. 22. The temperature of the cancerous cells are assumed to be 43° C.

First the cooling device 21 is activated (refer to 250 in FIG. 22) to sufficiently cool the water and the rotation frequency of the pump 222 is controlled to circulate the water at the minimum level by the information from the flow sensor 226 (refer to 252, 254 in FIG. 22). After the irradiation of the microwaves for a certain period of time (refer 256 in FIG. 22), the output of the magnetron 208 is shut off (refer to 258 in FIG. 22) and the temperature measurement inside the body starts using the temperature sensor 230 (refer to 260 in FIG. 22). After the temperature measurement, the temperature inside the body is compared to the temperature set by the operator in advance (in this embodiment, 43° C.) (refer to 262 in FIG. 22). If the inside temperature is lower than the set value, the rotation frequency is lowered one step to decrease the surface temperature (the minimum circulation is kept on to prevent burns on the body surface as shown by the reference numeral 264 in FIG. 22) and to heat cancerous cells to the set temperature by irradiating cells with microwaves by controlling the temperature from outside. When the temperature of cancerous cells becomes higher than the set value the irradiation is suspended until the temperature comes down below the set value, repeating measurement loop. The rotation frequency is increased one step at a time (FIG. 22, 268) using measurement intervals to bring down the surface temperature and to heat the cancerous cells to the set value rapidly by controlling from outside the body. In this embodiment, as in the first embodiment, time is measured from the time the temperature of cancerous cells of the heated region exceeds the set value (refer to 266 in FIG. 22) and ends when the time inputted by the operator expires (refer to 272 in FIG. 22).

FIG. 23 shows the temperature distribution at the cancerous cells heated by the method of this embodiment (A) and the temperature distribution by the conventional method (B). In this drawing, the interval during which the temperature is increasing represents the time of microwave irradiation and the decrease represents the measurement time during which the output of the magnetron is suspended. In the conventional method, flow of water which cools the body surface is not variable and the intermittent operation of the microwave oscillator is kept on even after the temperature exceeds the set temperature (43° C.) and heating is extremely inaccurate. In this embodiment, the desired temperature is achieved rapidly and if exceeds it will be cooled quickly thus keeping the temperature at 43° C. almost constantly.

Figure 25:
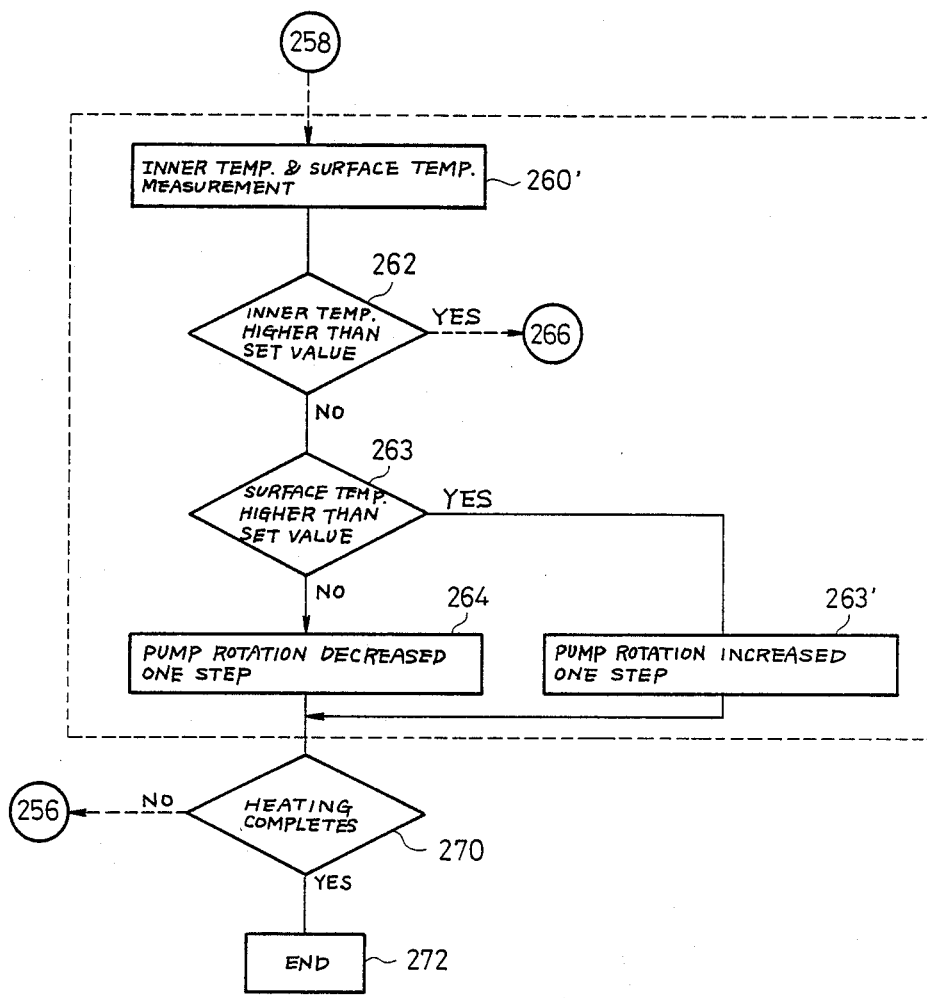
FIG. 25 is a flow chart showing the operation in FIG. 24.

If a more accurate control is desired, a temperature sensor 228 may be provided at the exhaust side of the cooling mechanism 234 of the applicator 220 to measure the surface temperature information of which is inputted to the main control 218 via the A/D converter and the control is performed as shown in the flow chart in FIG. 7 (FIG. 25 is the same as FIG. 22 except for changes made in the portion surrounded by dotted line). If the internal temperature is lower than the set value, the surface temperature (refer to 260' in FIG. 25) measured with the temperature sensor 228 is compared to the surface temperature set by the operator (refer to 263 in FIG. 25) and if the surface temperature is lower than the set value, the rotation frequency of the said pump is lowered one step (refer to 264 in FIG. 25) and if it is higher, the rotation frequency is raised one step (refer to 263' in FIG. 25).

Figure 24:
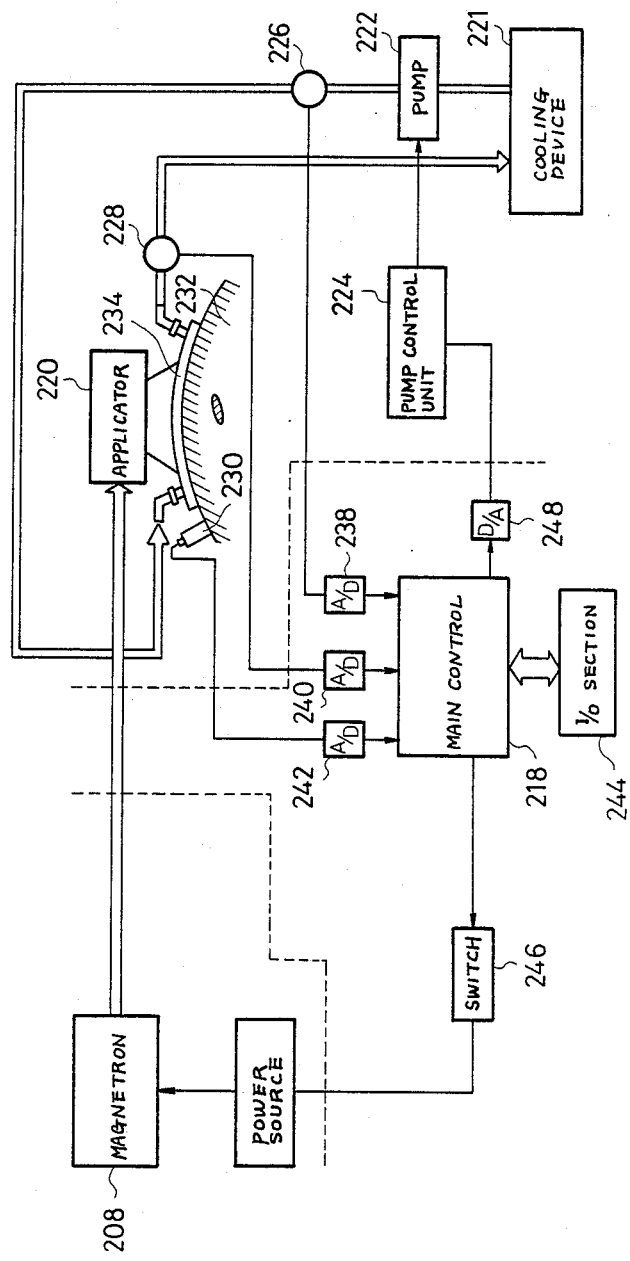
FIG. 24 is a system diagram showing a variation of the seventh embodiment.
Figure 26:
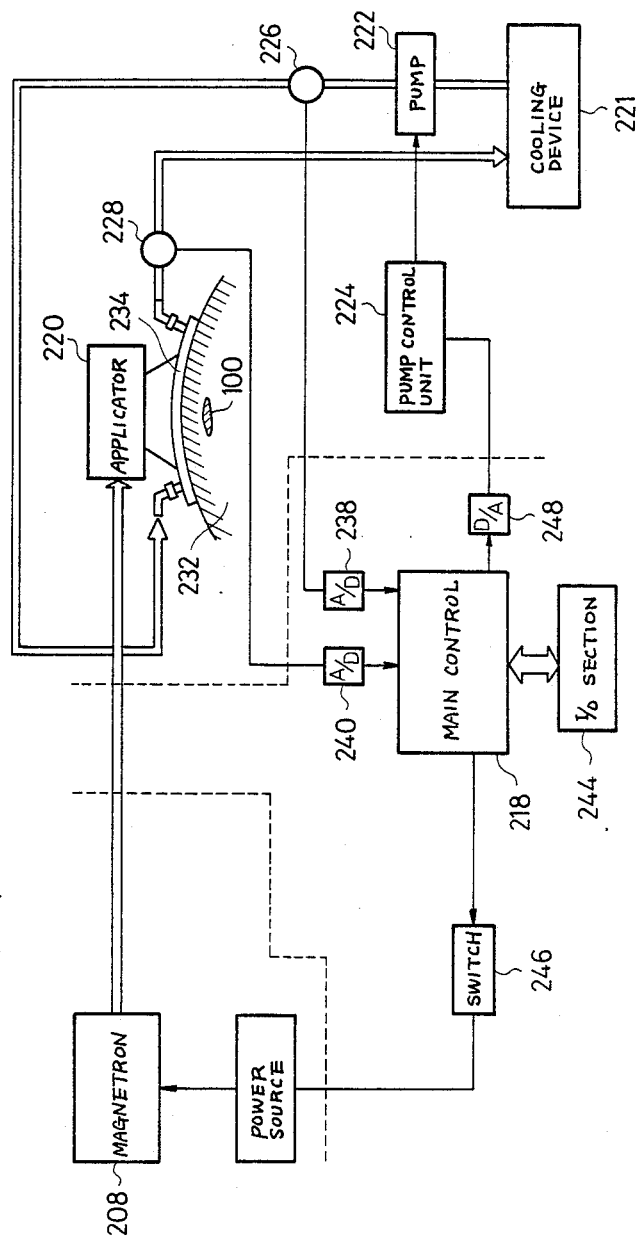
FIG. 26 is a system diagram showing another variation of the seventh embodiment.

If the cancerous region 100 is near the body surface, as shown in FIG. 26, heating is possible without inserting the temperature sensor shown in FIG. 24.

More specifically, if the cancerous growth is near the body surface the control of the flow of the cooling water may be done on the information from the surface sensor 228 rather than the inside sensor 230 since the temperatures of cancerous cells and body surface are considered to be almost the same (see FIG.. 27).

Figure 27:
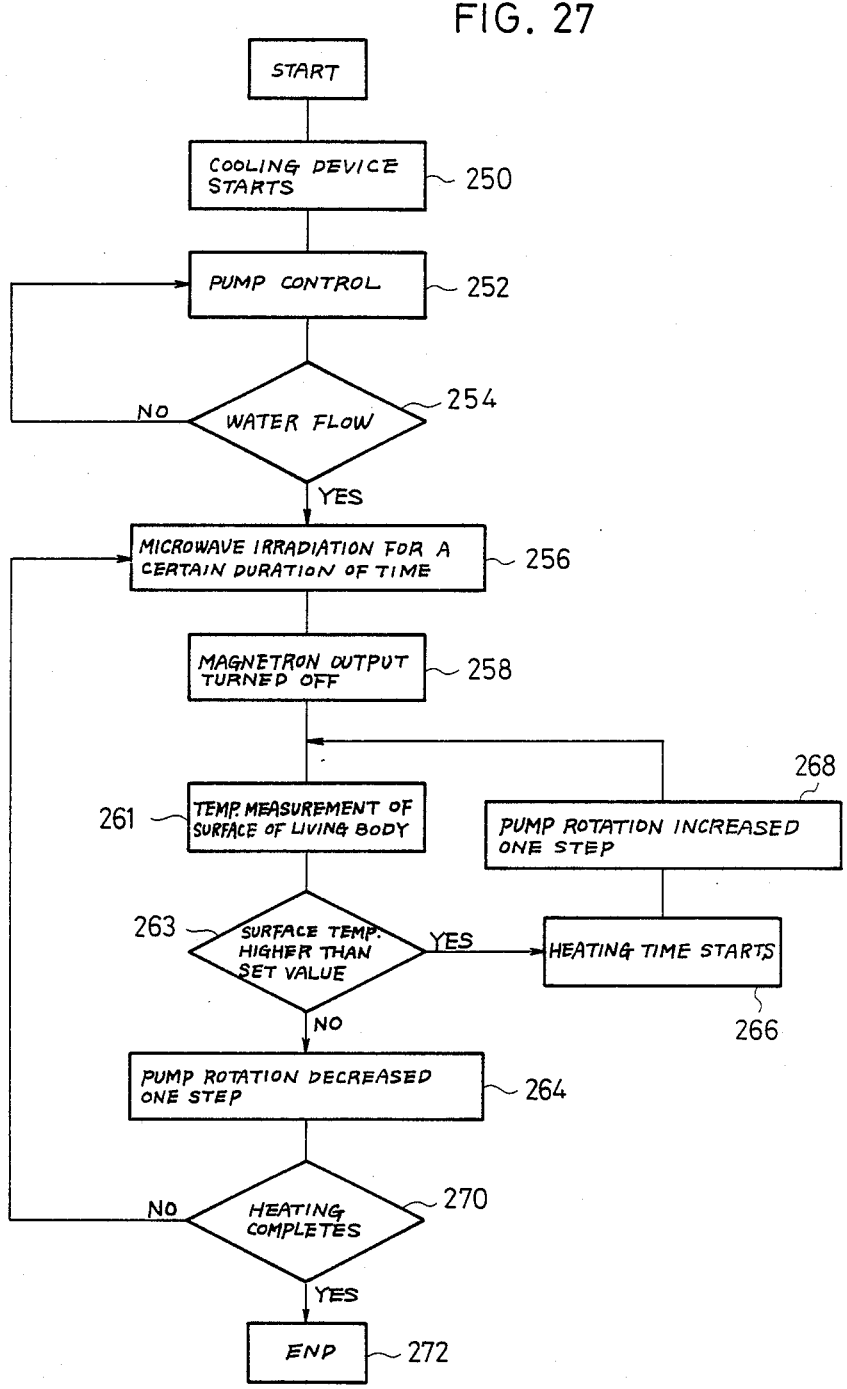
FIGS. 27 and 28 are flow charts showing the operation in FIG. 26.
Figure 28:
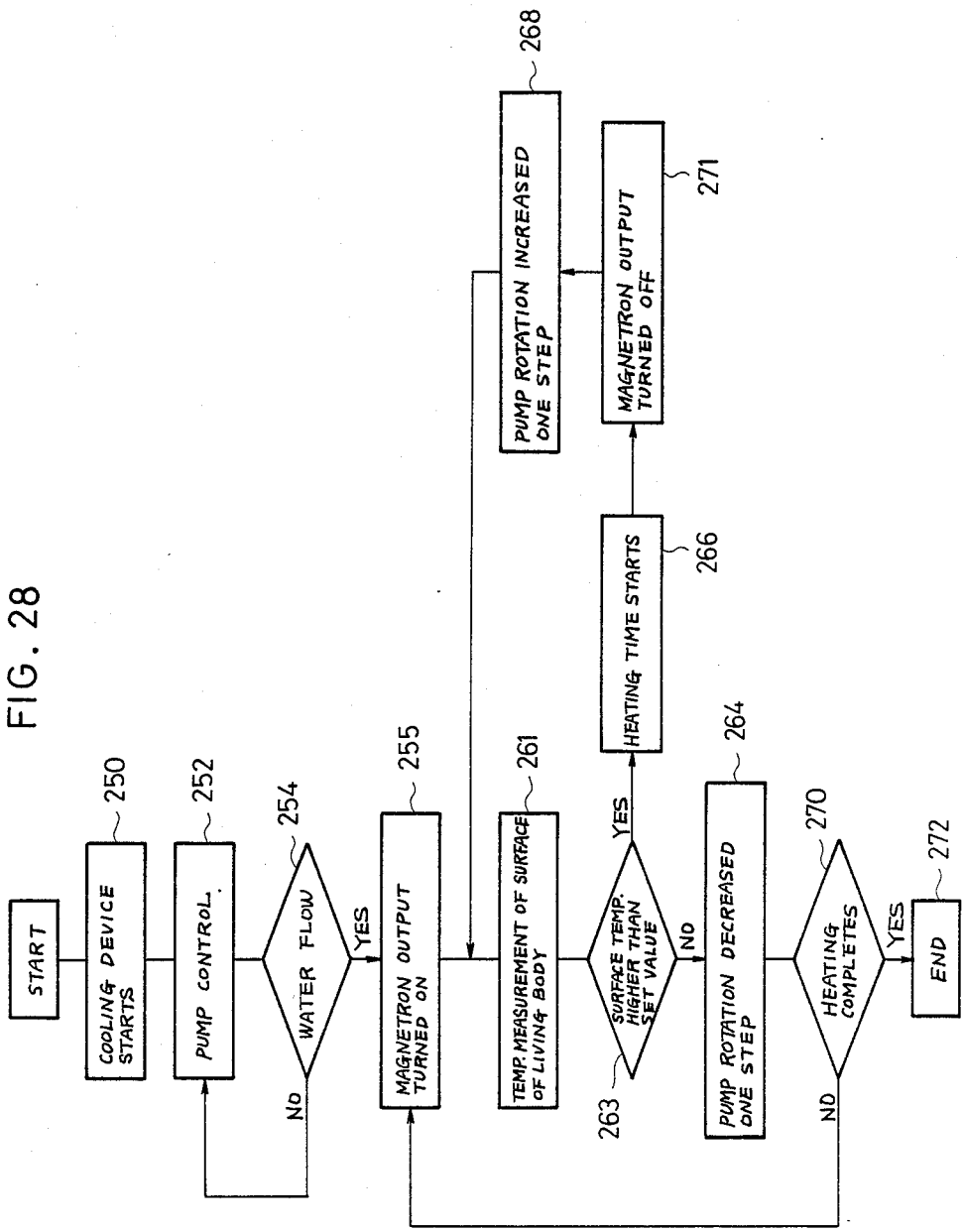

In this case, there is no need to shut off the output of the magnetron since the temperature sensor 228 is not affected by microwaves. In consequence, as shown in FIG. 28, the measurement of the surface temperature may done (refer to 255 in FIG. 28) and if the surface temperature is lower than the set value, the rotation frequency may be lowered (refer to 264 in FIG. 28) while continuing microwave irradiation, and if the surface temperature is higher than the set value the magnetron output may be shut off (refer to 271 in FIG. 28) and the pump rotation is raised one step (refer to 268 in FIG. 28), with the microwave irradiation off until the surface temperature comes down below the set value, while continuing the measurement loop. This method enables a more accurate heating of the subject region as compared with FIG. 27. The configuration may be made to make it possible to perform the temperature measurement while keeping the microwave irradiation as in the case of the second embodiment.

(Eighth Embodiment)

Figure 29:
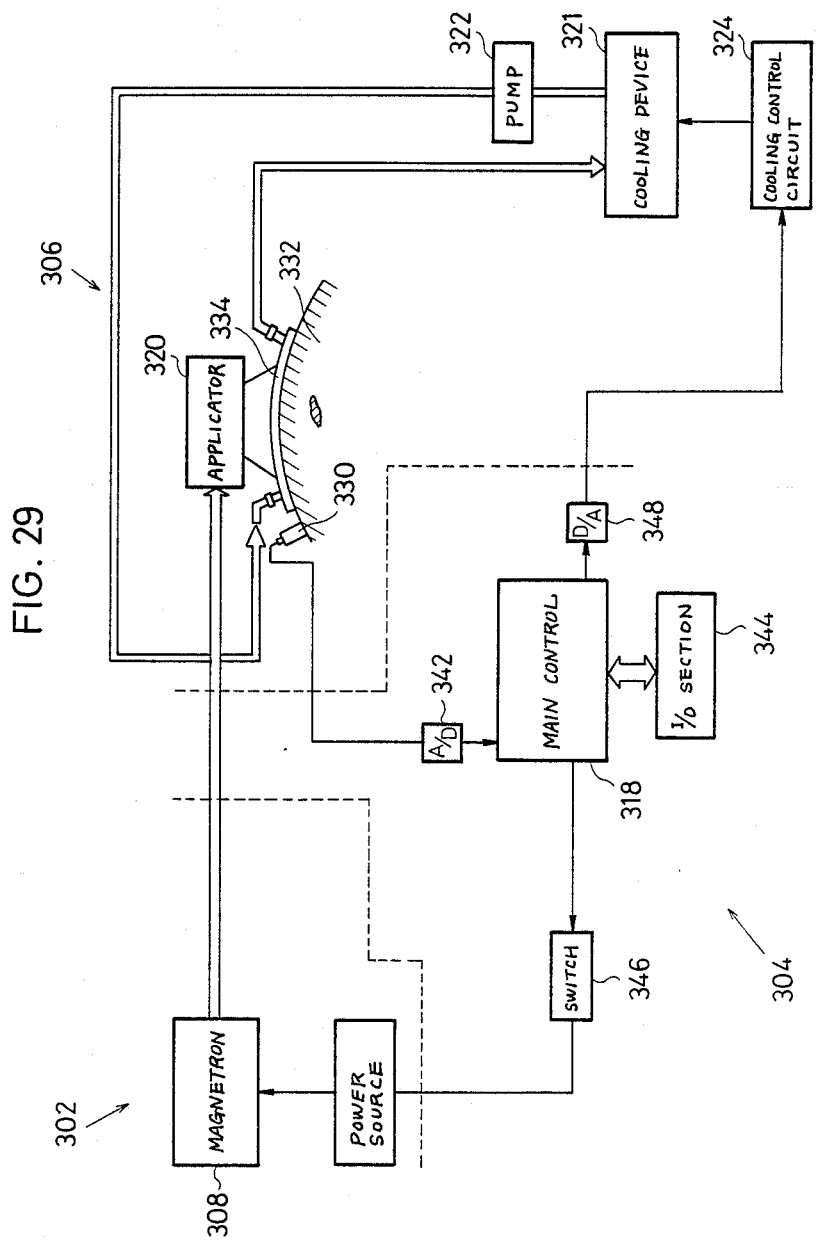
FIG. 29 is the entire system diagram of the eighth embodiment.
Figure 30:
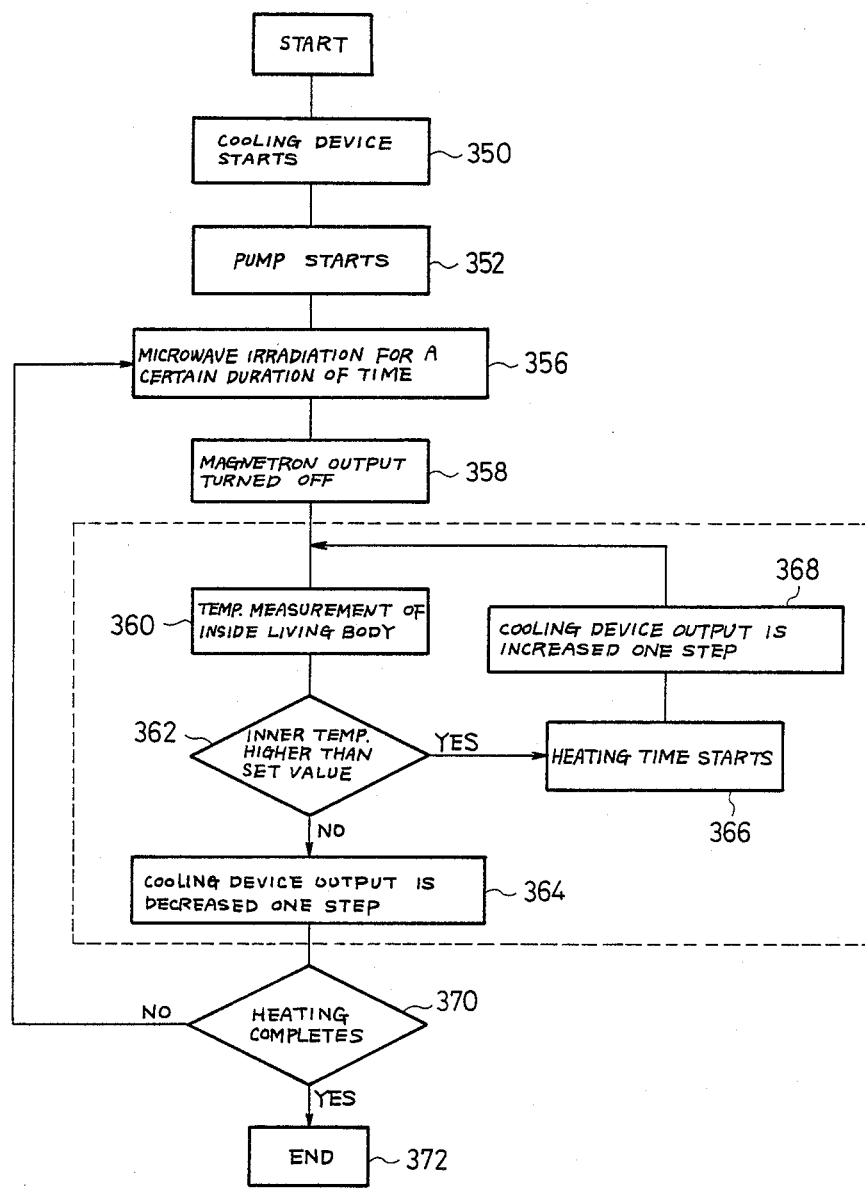
FIG. 30 is a flow chart showing the operation in FIG. 29.

FIGS. 29 and 30 show the eighth embodiment.

This method, as in the seventh embodiment, performs hyperthermia by keeping the output of the microwave generation means 302 at a constant level and by controlling cooling of the heated body surface. In this eighth embodiment a configuration is adopted in which the temperature of the cooling water is controlled to cool the body surface. The remainder of this configuration is the same as the seventh embodiment.

The overall operation and functions of the eighth embodiment are described referring to FIG. 30. Here, the temperature for cancerous region is assumed to be set at 43° C.

The cooling device 321 is activated (refer to 350 in FIG. 30) and when the water is sufficiently cooled, the pump 322 is operated (refer to 352 in FIG. 30). Then the microwave irradiation is performed for a certain time period (refer to 356 in FIG. 30), and the magnetron output is shut off (refer to 358 in FIG. 30) and temperature measurement with the sensor 330 follows (refer to 360 in FIG. 30). The irradiation is shut off during the temperature measurement because the microwave causes errors in the measurement with the sensor 330 inserted in the living body. After the temperature measurement, the value is compared with the set value inside the living body set by the operator (43° C. in this example) (refer to 362 in FIG. 30). If the internal temperature is lower than the set value, the output of the cooling device 321 (cooling effect) is lowered one step (the cooling device output may be turned off in this case, because the water circulated by the pump 322 prevents generation of heat layer in the surface layer of the living body) to raise the body surface temperature (refer to 364 in FIG. 30) thus accelerating the temperature rise of the cancerous cells. If, as a result, the temperature at cancerous region becomes higher than the set value, the microwave irradiation is suspended while keeping temperature measurement loop. During this measurement intervals the output of the cooling device 321 (cooling effect) is raised one step at a time (refer to 368 in FIG. 30) to cool the water which brings down the surface temperatures and in turn brings the temperature of the cancerous cells to the set value. Then in the same manner as the previously described seventh embodiment, time is measured from the time the temperature of the cancerous growth exceeds the set value (refer to 366 in FIG. 30) and ends when the heating time inputted by the operator expires (refer to 372 in FIG. 30). Even in this method, the result which is almost the same as in the case of the seventh embodiment is obtained.

Figure 31:
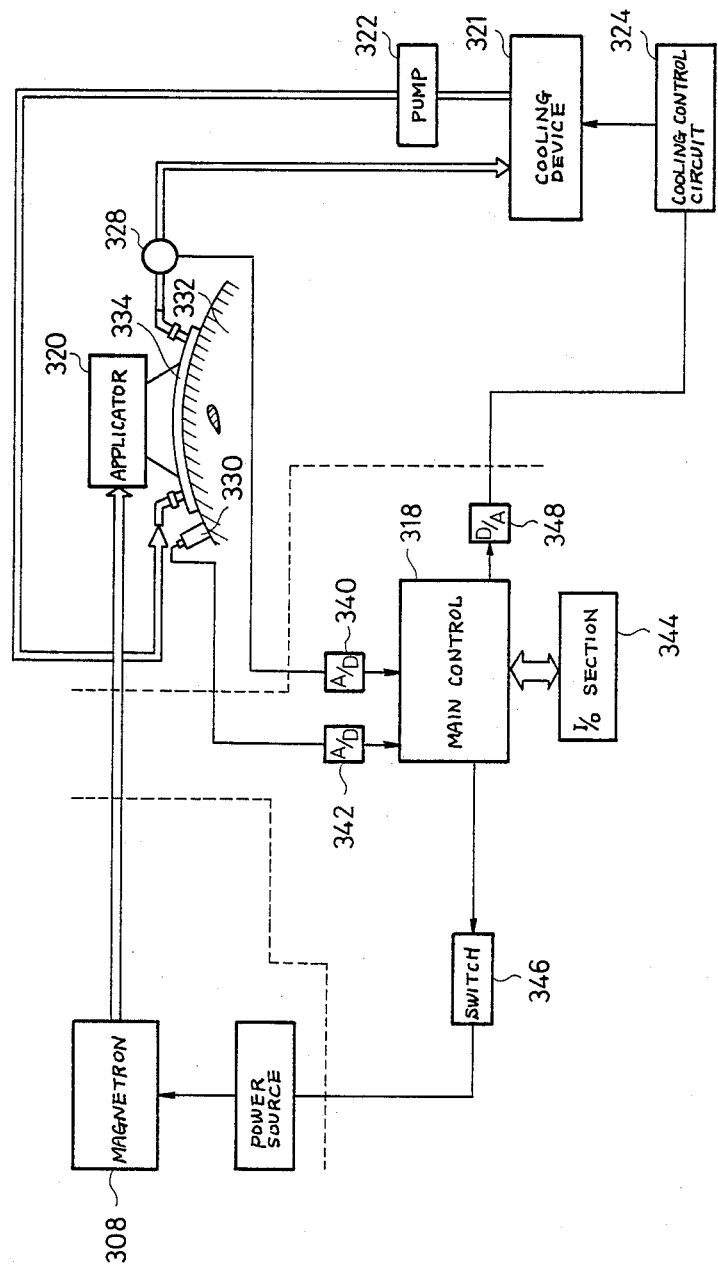
FIG. 31 shows system diagram of a variation of the eighth embodiment.
Figure 32:
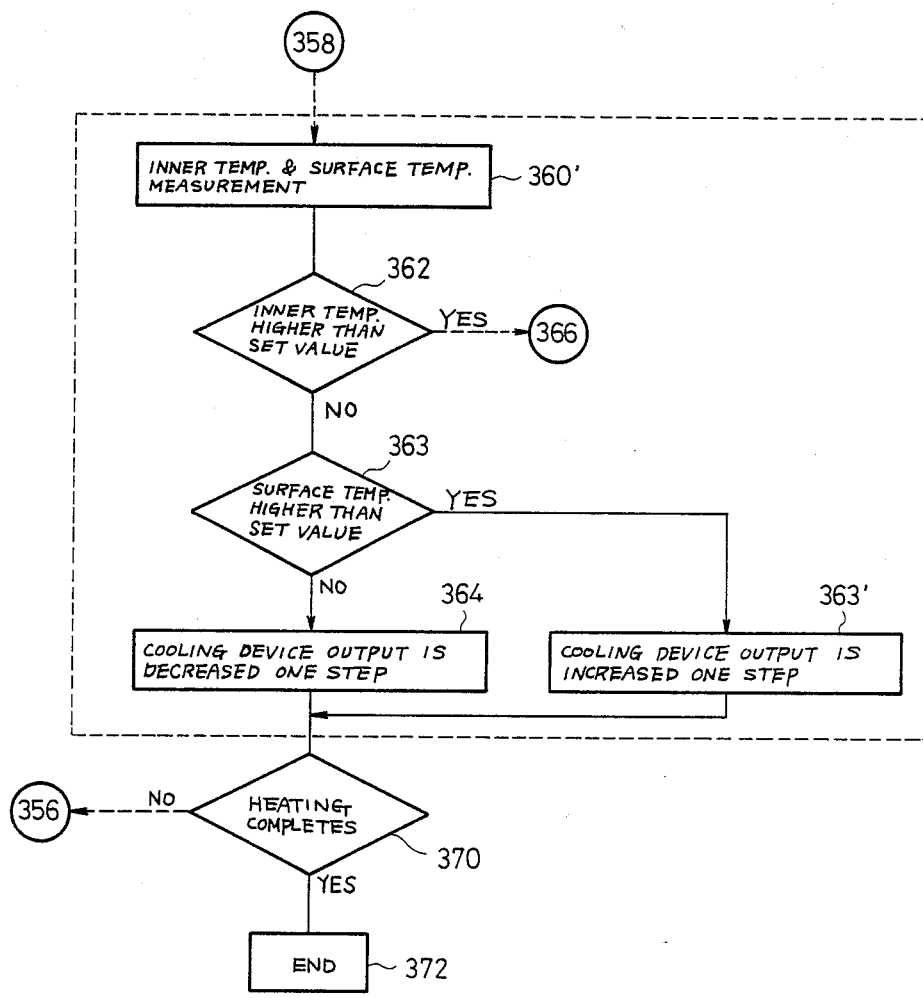
FIG. 32 is a flow chart showing the operation in FIG. 31.
Figure 33:
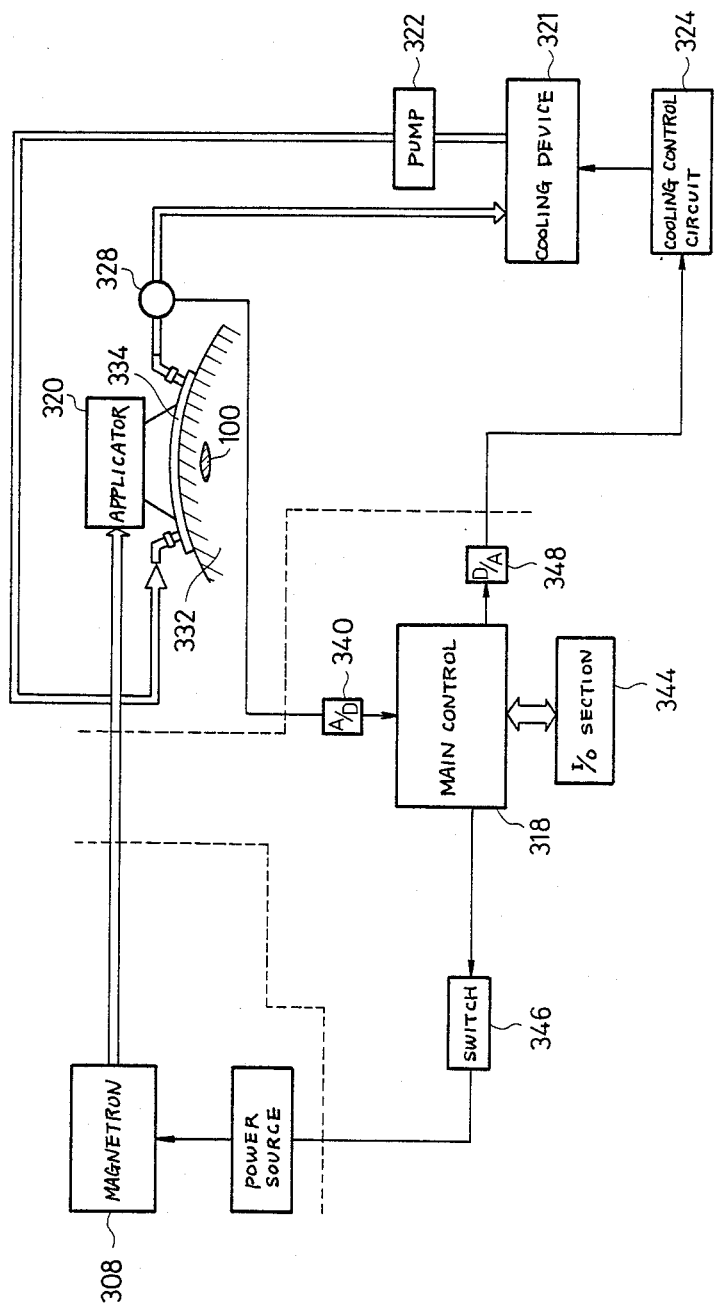
FIG. 33 is a system diagram showing an another variation of the eighth embodiment.

In the above described embodiment, if a more accurate control is desired, as shown in FIG. 31, a temperature sensor 328 is provided on the exhaust side of the cooling mechanism 334 of the applicator 320, whereby the surface temperature is measured and its information is fed to the main control 318 via the A/D converter to perform the control as shown in a flow chart of FIG. 32 (FIG. 32 is the same as FIG.. 30 except for a portion of the flow chart surrounded by dotted lines). If the internal temperature is lower than the set value, the surface temperature (refer to 360' in FIG. 32) measured by the temperature sensor 328 and the surface temperature set by the operator are compared (refer to 363 in FIG. 32) and if the surface temperature is lower than the set value, the output of the cooling device 321 (cooling effect) is lowered one step (refer to 364 in FIG. 32), and if the surface temperature is higher the output of the cooling device (cooling effects) is raised one step (refer to 363' in FIG. 32).

Figure 34:
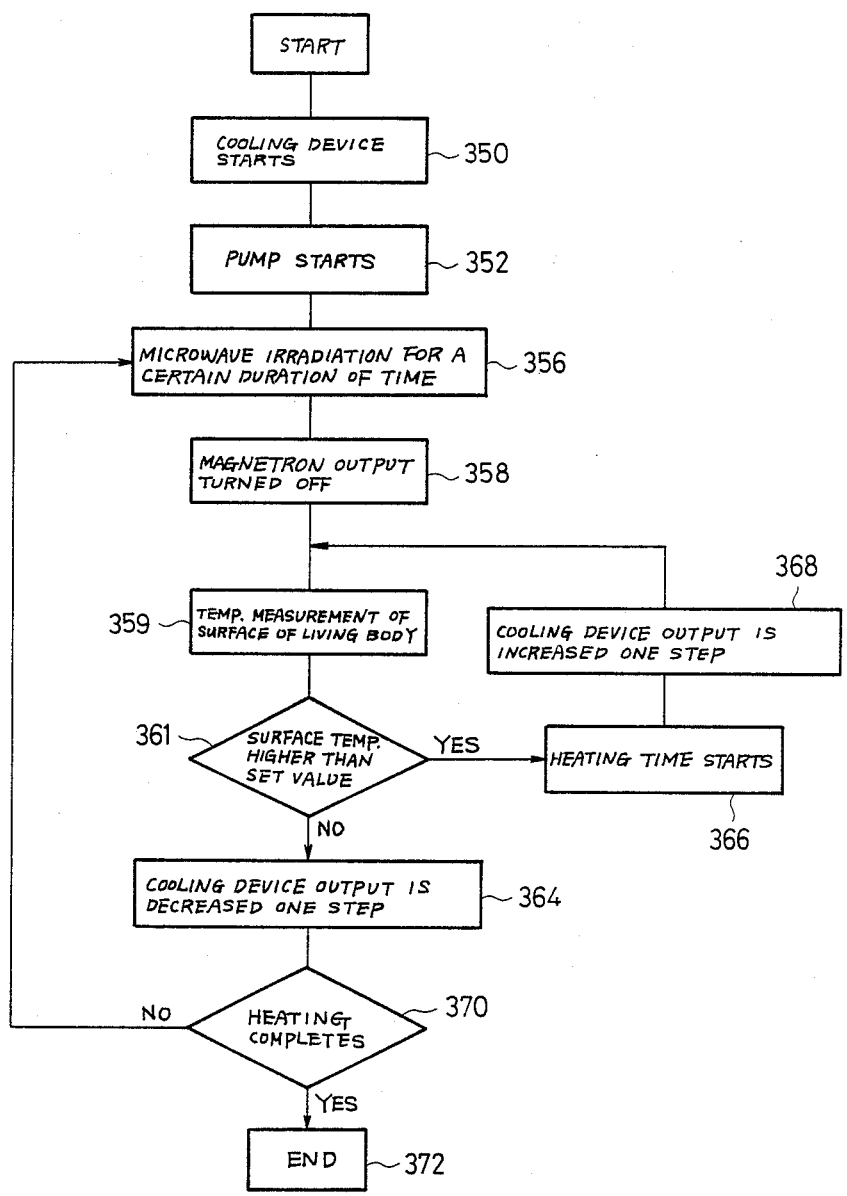
FIGS. 34 and 35 are flow charts of the operation in FIG. 33.

If the cancerous cells 100 are near the body surface, heating becomes possible without inserting the temperature sensor 330. Since the temperatures are almost the same at the cancerous cells and the surface, the body surface temperature sensor 328, rather than the sensor inserted in the living body, gives information for controlling the output (cooling effect) of the cooling device 321 (refer to FIG. 34).

Figure 35:
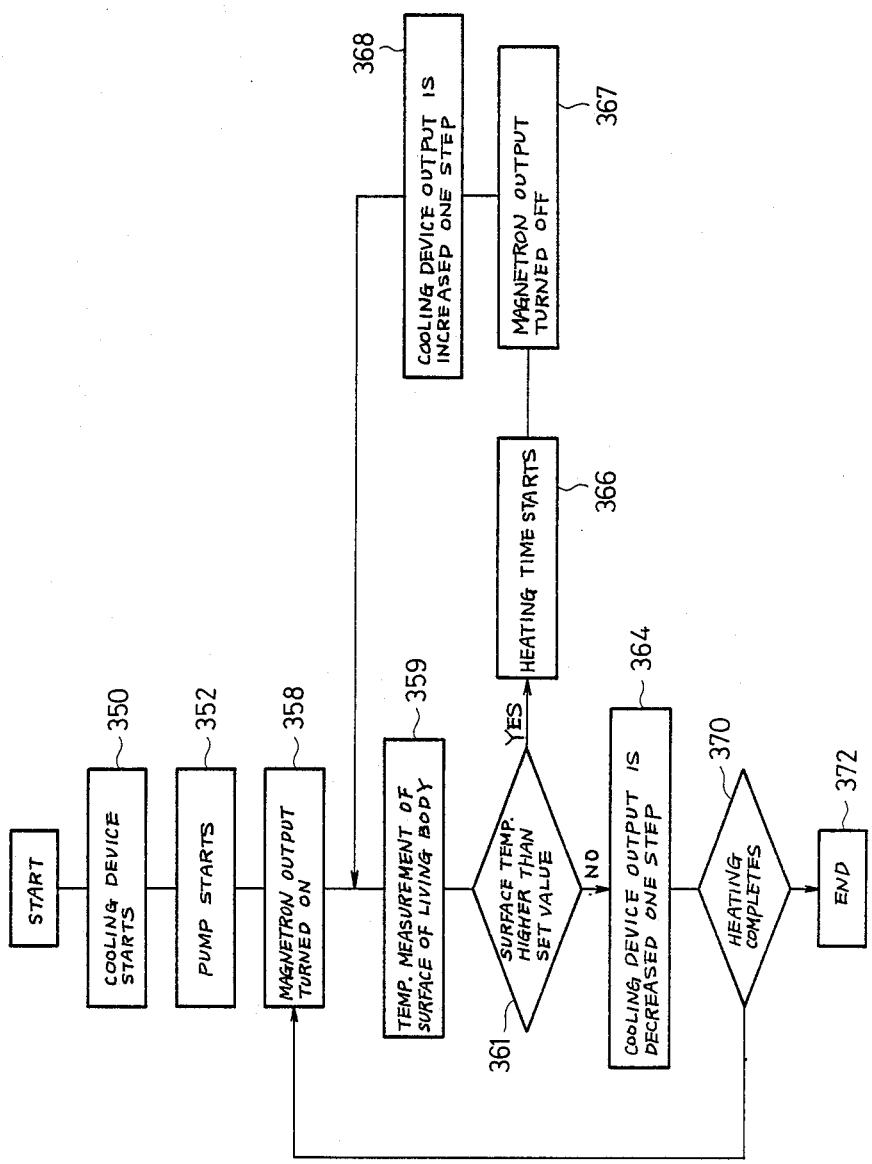

In this case the magnetron output need not be turned off during temperature measurement since the temperature sensor 328 is not affected by microwaves. In this case, as shown in FIG. 35, after the magnetron output is turned on temperature measurement of the body surface is made (refer to 359 in FIG. 35) and if the surface temperature is lower than the set value, the cooling device output (cooling effect) is lowered (refer to 364 in FIG. 35) while the microwave irradiation is continued, and when the surface temperature exceeds the set temperature the magnetron output 308 is shut off (refer to 367 in FIG. 35) and the cooling device 321 output (cooling effect) is raised one step (refer to 368 in FIG. 35) and the loop is repeated without performing irradiation. This method facilitates more accurate heating of the subject region compared to the method described in FIG. 34.

Eight examples of the present invention disclosed above are the hyperthermia treatment methods which utilize electromagnetic waves featuring an advantage of maintaining heating temperature highly accurate within a certain range.

What is claimed is:

1. A hyperthermia device for treating a region of a body comprising:
    (a) a selectively operable microwave generator having an adjustable power level for producing microwaves;
    (b) an applicator responsive to microwaves produced by the generator for directing the microwaves into said region thereby heating the same;
    (c) a temperature sensor for measuring the temperature of the body;
    (d) adjustable power level control means for effecting step-wise changes in the power level of the produced microwaves;
    (e) means for selecting a set value of temperature of the body;
    (f) control means responsive to said temperature sensor for periodically measuring the temperature of the body and for periodically causing said adjustable power level control means to step-wise increase the power level if the measured temperature is less than the set value and to decrease the power level if the measured temperature is greater than the set value;
    (g) means for starting the timing of a heating cycle during which the temperature of said region is held at said set value of temperature for a preselected time in response to the first time the measured temperature exceeds the set temperature;
    (h) means for operating said generator for a fixed period of time in response to either selection of a set value of temperature or a temperature measurement less than said set value; and
    (i) means for terminating the operation of said microwave generator at the end of said heating cycle 2. A hyperthermia device according to claim 1 including means to set a maximum power level, the control means being constructed and arranged to terminate operation of the generator when the measured temperature exceeds the set temperature and the actual power level of the generator is greater than or equal to the set maximum power level.

3. A method for performing hyperthermia therapy on a body comprising the steps of:
    (a) selecting a set value of temperature for the body;
    (b) applying to the body in initial burst of microwaves at a predetermined power level for a predetermined period of time;
    (c) measuring the temperature of the body at the termination of the burst;
    (d) comparing the measured temperature to the set temperature;
    (e) applying to the body subsequent burst of microwaves, each burst lasting for said predetermined period of time and having a power level greater than the power levels of the preceding burst if the measured temperature is less than the set temperature, or less than the power level of the preceding burst if the measured temperature is greater than the set temperature;
    (f) starting the timing of the heating cycle of a preselected duration when the measured temperature exceeds said set value for the first time; and
    (g) terminating the application of microwaves to the body at the end of said heating cycle.

4. A method for performing hyperthermia therapy on a body comprising the steps of:
    (a) establishing the power level setting of a microwave generator at a maximum value;
    (b) operating the generator at said maximum power level setting to apply microwaves to the body;
    (c) terminating the operation of the microwave generator when the temperature of the body exceeds a preselected temperature;
    (d) periodically measuring the temperature of the body while the microwave generator is turned off, and incrementally decreasing the power level setting of the microwave generator until the temperature of the body no longer exceeds the preselected temperature thereby marking the start of a heat cycle of predetermined duration and establishing the current power level setting;

(e) operating the microwave generator for a fixed period of time at its current power level setting and thereafter terminating operation of the microwave generator;

(f) measuring the temperature of the body after the operation of the microwave generator terminates;

(g) incrementally increasing the power level of the microwave generator if the temperature of the body is less than said preselected temperature; and (h) repeating steps (d) through (f) until the end of said heating cycle.

5. A method for performing hyperthermia therapy on a region of a body utilizing a microwave generator that has a stepwise variable power level for applying bursts of microwaves to said region, said method comprising the steps of:

(a) periodically measuring the temperature of the region of the body;

(b) selecting a maximum value of a temperature for the region of the body;

(c) periodically comparing the measured temperature to the selected temperature during the absence of the application of microwaves to said region;

(d) causing said generator to apply an initial burst of microwaves at maximum power level to said region after the selection of a maximum value of temperature;

(e) starting the timing of a heating cycle of a preselected duration when the measured temperature exceeds said maximum value of temperature for the first time;

(f) reducing the power level of the generator by one step each time step (c) is carried out if the measured temperature is greater than the selected maximum value, and increasing the power level of the generator by one step each time step (c) is carried out if the measured temperature is less than the selected maximum value; and (g) causing the generator to apply a subsequent burst of microwaves at the current power level of the generator only if the comparison of step (c) is such that the measured temperature is less than said maximum value, and the heating cycle has not expired.

* * * * *

UNITED STATES PATENT AND TRADEMARK OFFICE
CERTIFICATE OF CORRECTION

PATENT NO. : 4,884,580

DATED : December 5, 1989

INVENTOR(S) : M. KIKUCHI et al.

It is certified that error appears in the above-identified patent and that said Letters Patent is hereby corrected as shown below:

Column 1, line 44, insert ---is--- before "unfit".
Column 1, line 58, change "temperatures" to ---temperature---.
Column 2, line 51, delete "an" after "showing".
Column 5, line 49, change "Refer" to ---refer---.
Column 5, line 49, change "in" to ---is---.
Column 5, line 61, change "microwave" to ---microwaves---.
Column 6, line 11, delete "said".
Column 6, line 12, change "wave" to ---waves---.
Column 7, line 45, change "circulated" to ---circulate---.
Column 7, line 46, change "136" to ---122---.
Column 7, line 47, change "20" to ---120---.
Column 8, line 3, change "116" to ---140---.
Column 8, line 25, change "22" to ---122---.
Column 8, line 32, change "44" to ---144---.
Column 8, line 63, change "give" to ---gives---.
Column 9, line 20, change "s" to ---is---.
Column 10, lines 8/9, change "compare" to ---compared---.
Column 10, line 18, change "164, 166" to ---167, 169---.
Column 10, line 61, change "21" to ---221---.
Column 11, line 40, change "exceeds" to ---exceeded---.
Column 12, line 5, insert ---be--- after "may".
Column 12, line 5, change "255" to ---261---.
Column 14, line 21, insert ---.--- after "cycle".
Column 14, line 32, change "in" to ---an---.
Column 14, line 39, change "burst" to ---bursts---.

UNITED STATES PATENT AND TRADEMARK OFFICE
CERTIFICATE OF CORRECTION

PATENT NO. : 4,884,580

DATED : December 5, 1989

INVENTOR(S) : M. KIKUCHI et al.

It is certified that error appears in the above-identified patent and that said Letters Patent is hereby corrected as shown below:

Column 14, line 42, change "levels" to ---level---.

Signed and Sealed this

Twenty-second Day of September, 1992

Attest:

*Attesting Officer*

DOUGLAS B. COMER

*Acting Commissioner of Patents and Trademarks*